(12) United States Patent
Bockelmann et al.

(10) Patent No.: US 7,908,088 B2
(45) Date of Patent: Mar. 15, 2011

(54) METHOD FOR ELECTRONICALLY DETECTING AT LEAST ONE SPECIFIC INTERACTION BETWEEN PROBE MOLECULES AND TARGET BIOMOLECULES

(75) Inventors: Ulrich Bockelmann, Paris (FR); François Pouthas, Heidelberg Allemagne (FR); Cédric Gentil, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 1281 days.

(21) Appl. No.: 10/538,062

(22) PCT Filed: Jul. 4, 2003

(86) PCT No.: PCT/FR03/02091
§ 371 (c)(1),
(2), (4) Date: Apr. 10, 2006

(87) PCT Pub. No.: WO2004/057027
PCT Pub. Date: Jul. 8, 2004

(65) Prior Publication Data
US 2006/0246443 A1 Nov. 2, 2006

(30) Foreign Application Priority Data
Dec. 11, 2002 (WO) .................. PCT/FR02/04283

(51) Int. Cl.
*G01N 33/48* (2006.01)
(52) U.S. Cl. .......................................... 702/19
(58) Field of Classification Search ........ 702/19
See application file for complete search history.

(56) References Cited

U.S. PATENT DOCUMENTS

| | | | |
|---|---|---|---|
| 4,238,757 A | 12/1980 | Schenck | |
| 5,164,319 A | 11/1992 | Hafeman et al. | |
| 5,242,793 A | 9/1993 | Kariyone et al. | |
| 5,466,348 A | 11/1995 | Holm-Kennedy | |
| 5,496,699 A | 3/1996 | Sorenson | |
| 5,498,521 A | 3/1996 | Dryja et al. | |
| 5,653,939 A | 8/1997 | Hollis et al. | |
| 5,805,014 A * | 9/1998 | Price | 327/427 |
| 5,922,591 A * | 7/1999 | Anderson et al. | 435/287.2 |
| 6,203,981 B1 | 3/2001 | Ackley et al. | |
| 6,281,006 B1 | 8/2001 | Heller et al. | |
| 6,322,963 B1 | 11/2001 | Bauer | |
| 6,331,274 B1 | 12/2001 | Ackley et al. | |
| 2001/0024788 A1 | 9/2001 | Hashimoto | |
| 2003/0190608 A1 | 10/2003 | Blackburn | |
| 2004/0238379 A1* | 12/2004 | Lindsay et al. | 205/792 |

FOREIGN PATENT DOCUMENTS

| | | |
|---|---|---|
| WO | 00/75276 | 12/2000 |
| WO | 03/052097 | 6/2003 |
| WO | 03/054225 | 7/2003 |

OTHER PUBLICATIONS

Souteyrand, E. et al.: "Direct Detection of the Hybridization of Synthetic Homo-Oligomer DNA Sequences by Field Effect" J. Phys. Chem., vol. 101, pp. 2980-2985, 1997. XP-001040796.

Tsuruta, Hitoshi et al.: "Detection of the products of polymerase chain reaction by an ELISA system based on an ion sensitive field effect transistor" Journal of Immunological Methods, vol. 176, pp. 45-52, 1994. XP009021947.

Nakamura, M. and Yano, M.: "Oline pH, $pCO2$ and $pO2$ monitoring system using two-way cyclic pumping of lactate Ringer as a baseline solution" Medical & Biological Engineering & Computing, vol. 25, pp. 45-50, Jan. 1987. XP-001156254.

Kiessling, Volker et al.: "Extracellular Resistance in Cell Adhesion Measured with a Transistor Probe" Langmuir, vol. 16, pp. 3517-3521, 2000. XP-001040795.

* cited by examiner

*Primary Examiner* — Jerry Lin
(74) *Attorney, Agent, or Firm* — Oblon, Spivak, McClelland, Maier & Neustadt, L.L.P.

(57) ABSTRACT

The invention concerns a method for detecting at least one specific interaction between probe molecules and target biomolecules fixed to at least one active zone of a sensor. Said sensor consists of an array of field-effect transistors (T1, T2,), each of which has a gate region constituting an active zone (3) whereon said specific interaction is to be detected.

17 Claims, 20 Drawing Sheets

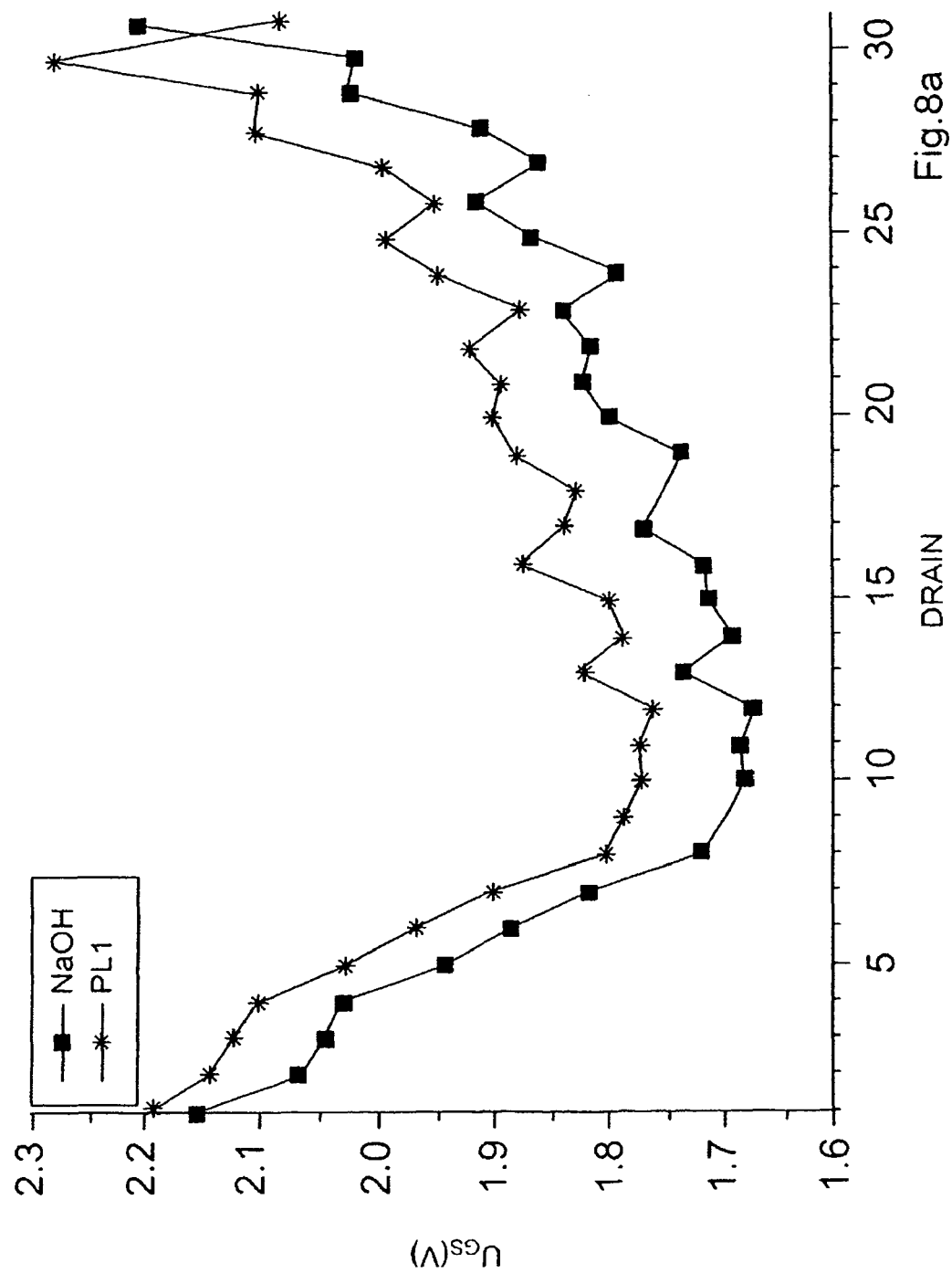

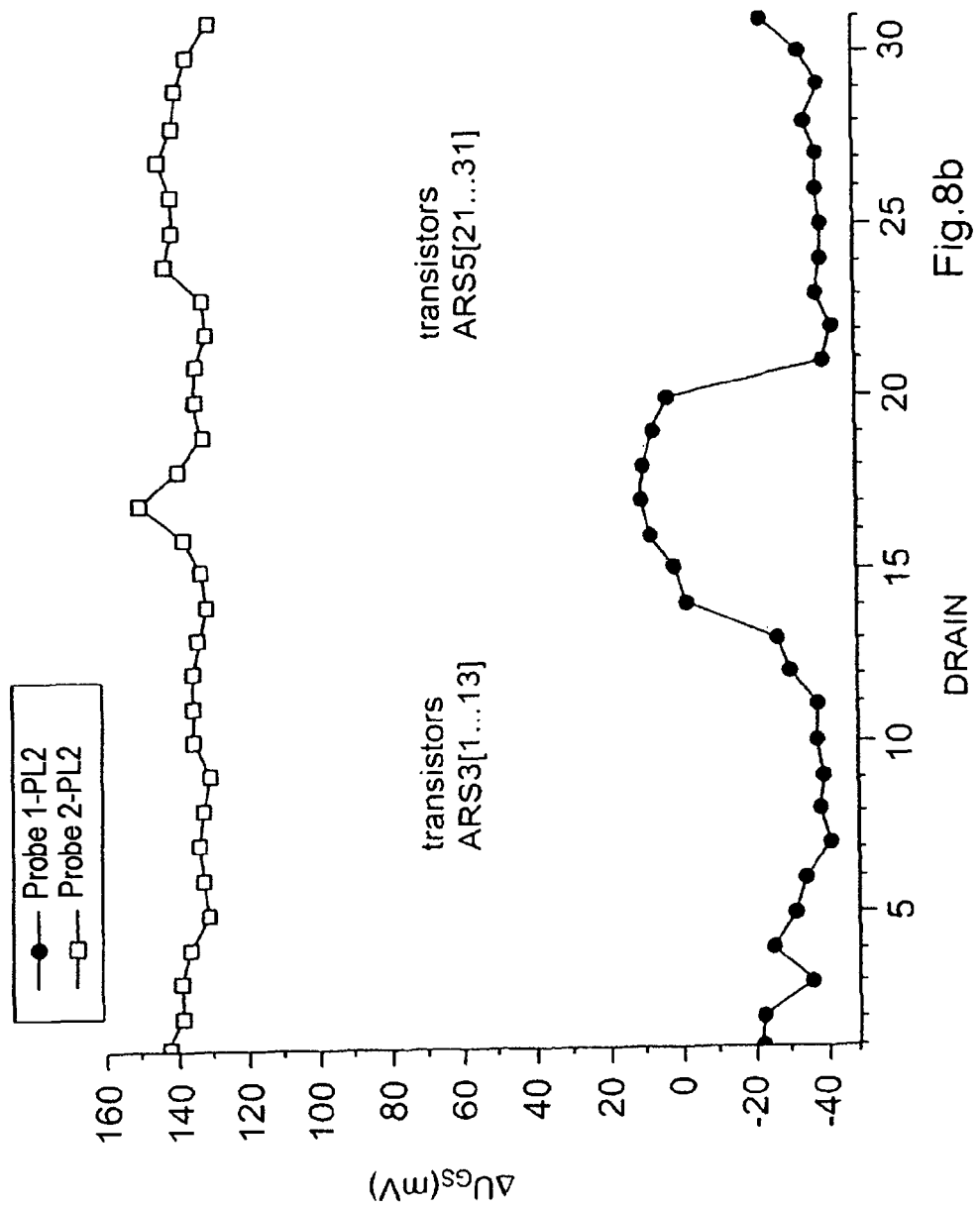

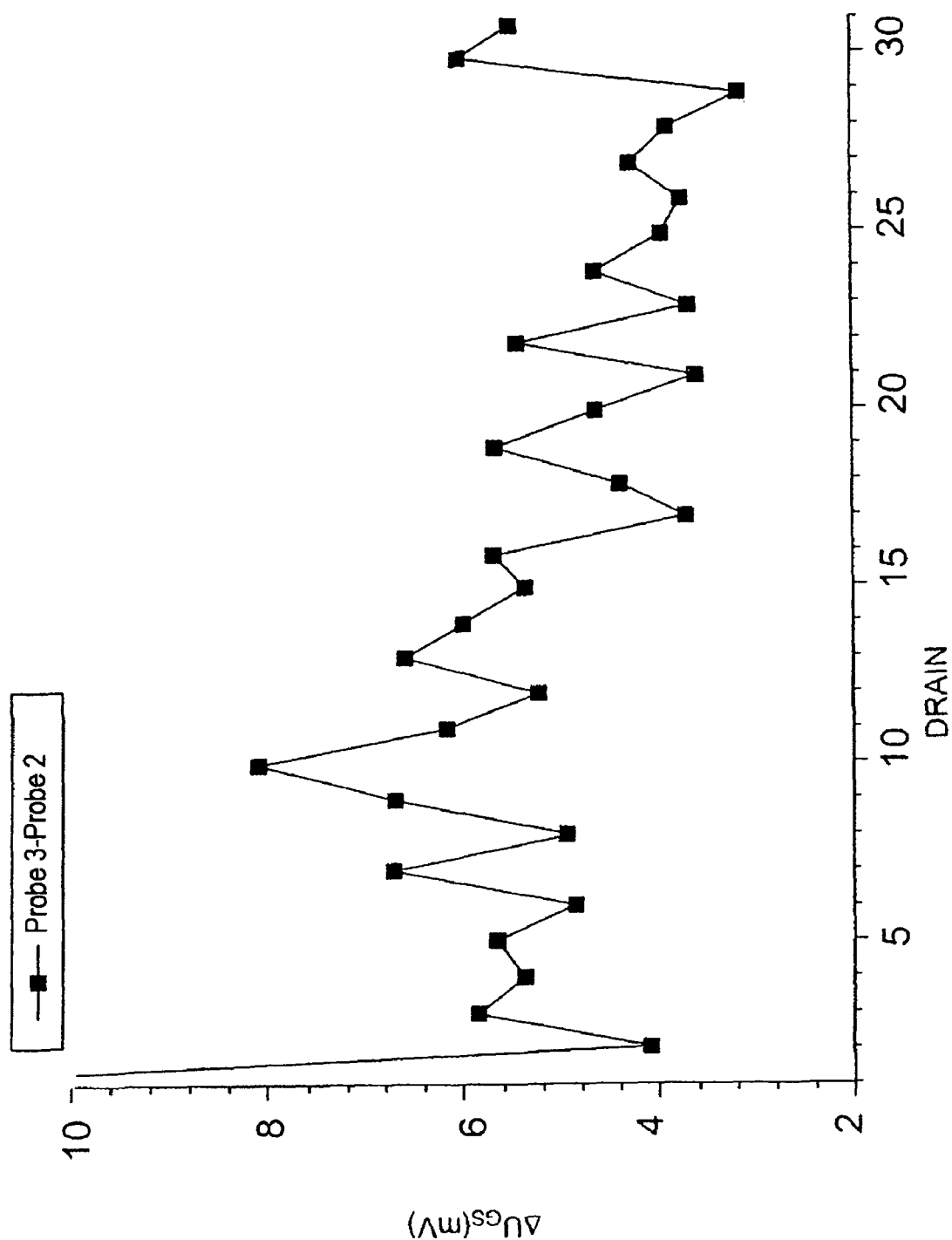

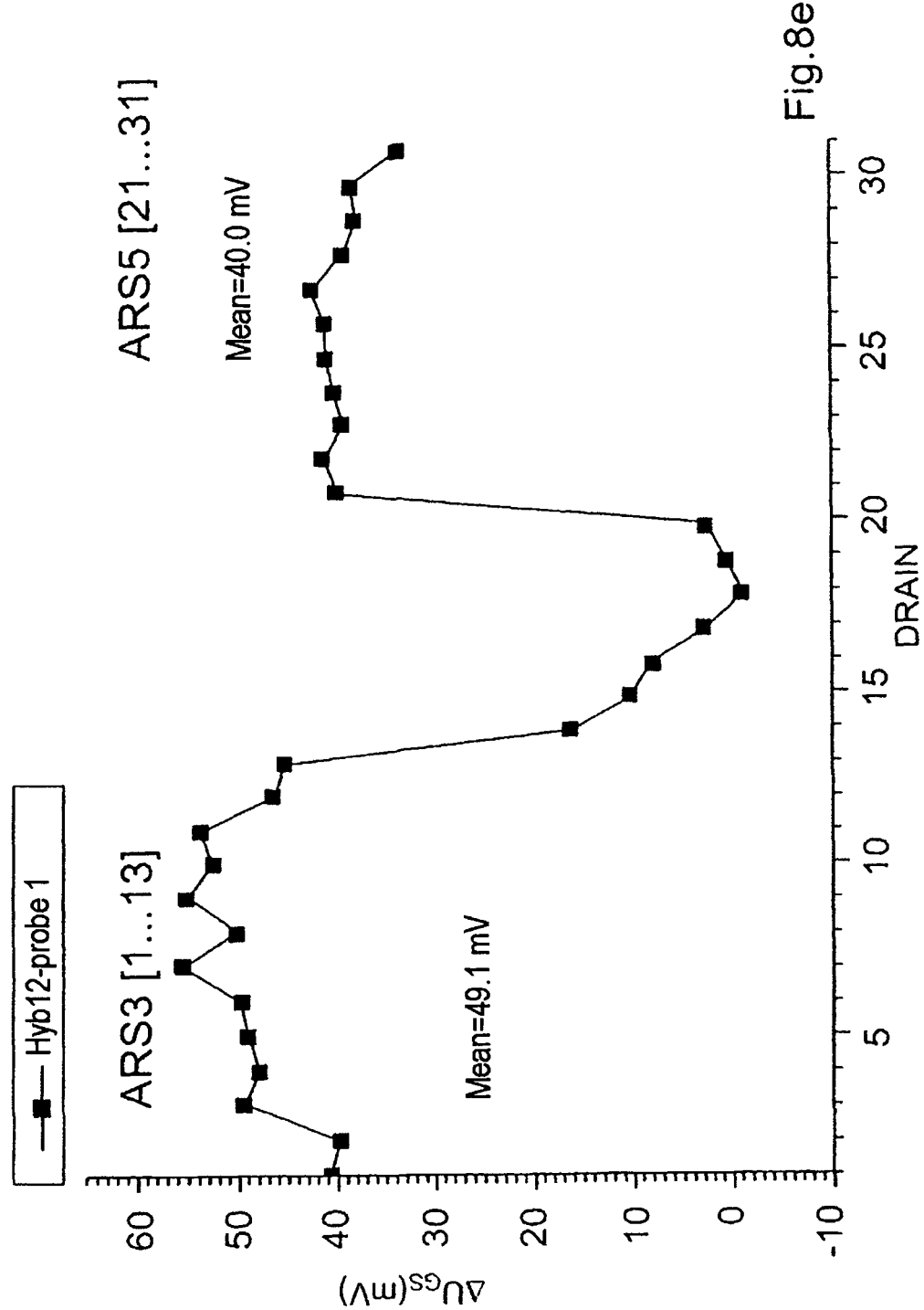

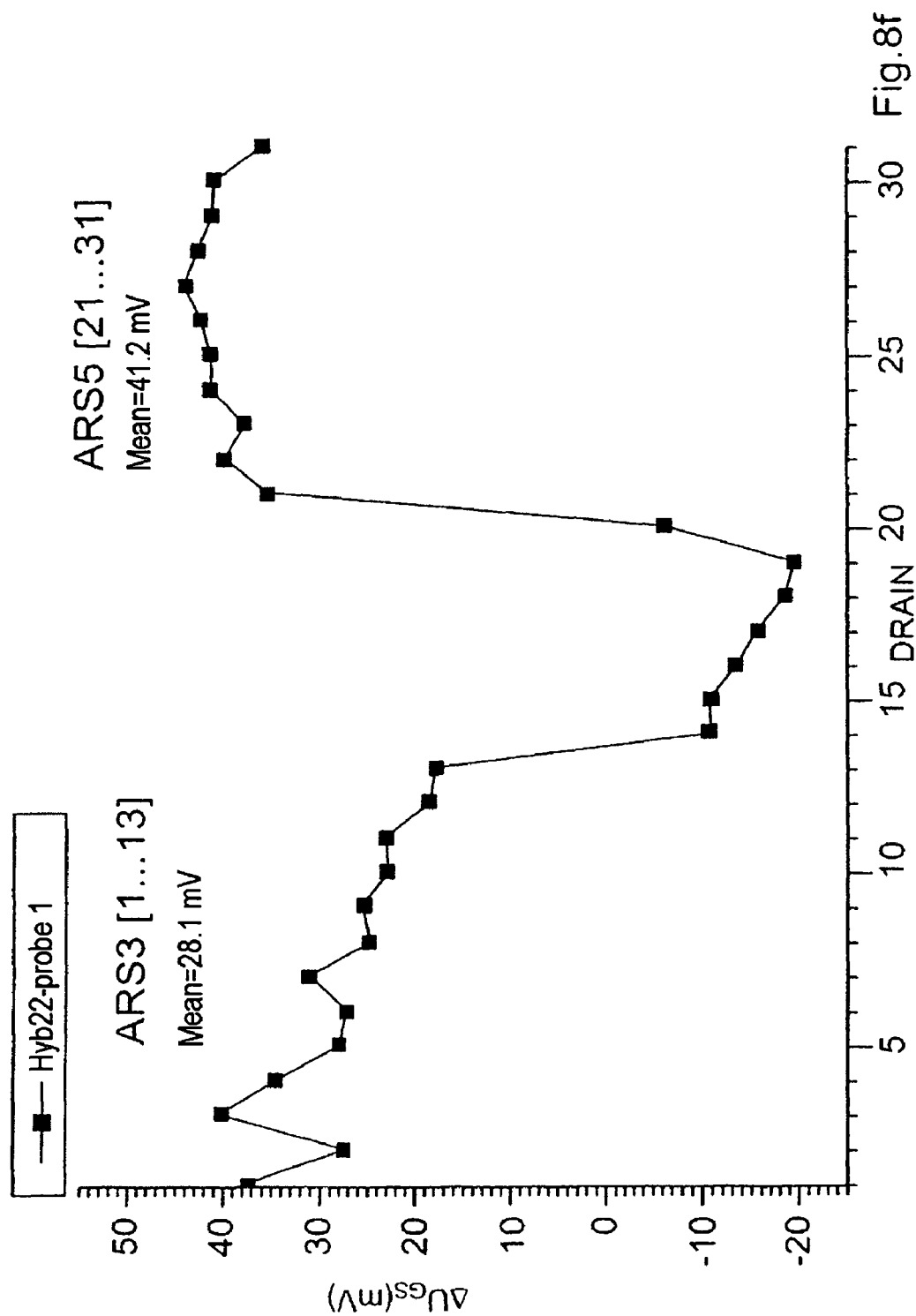

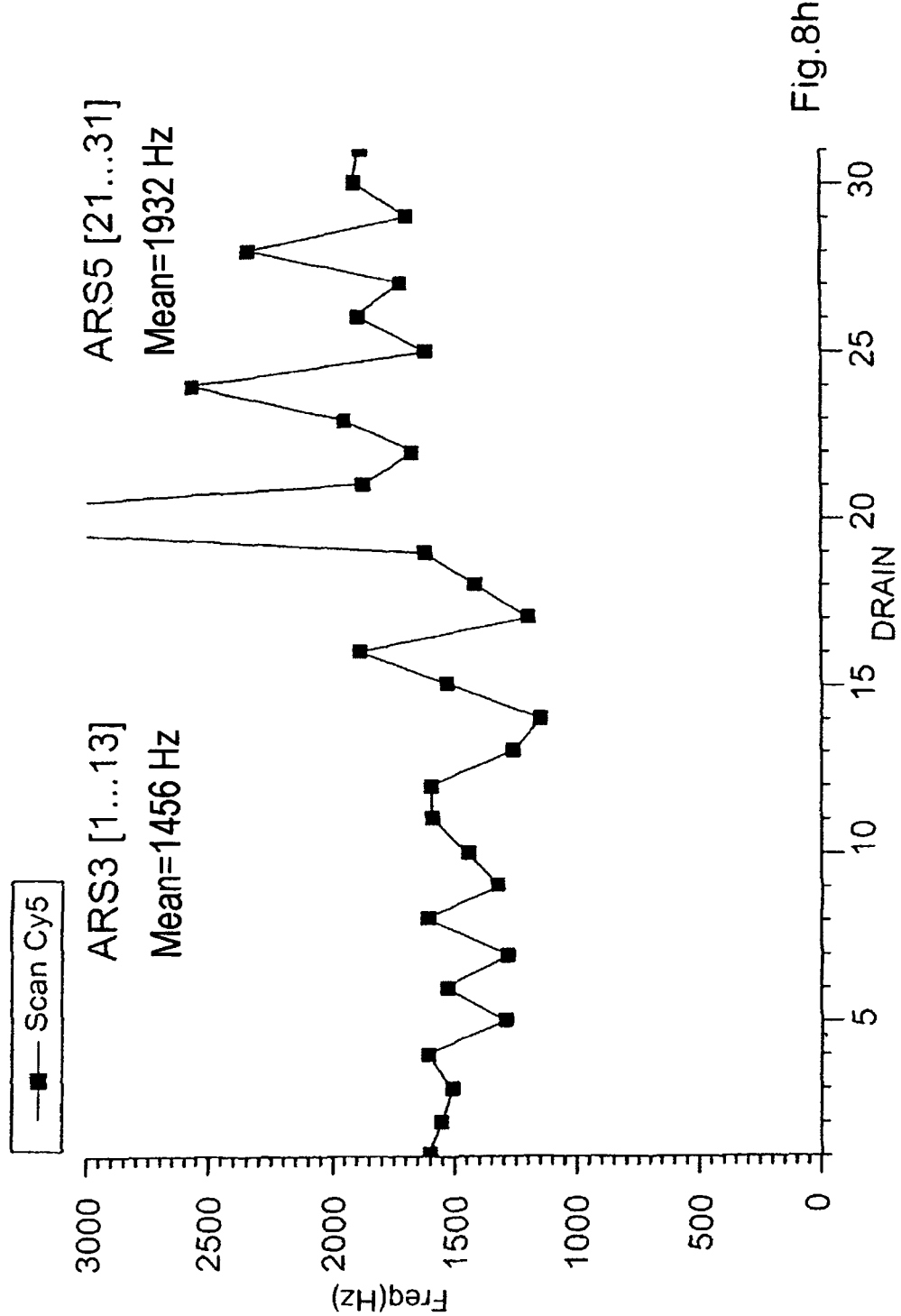

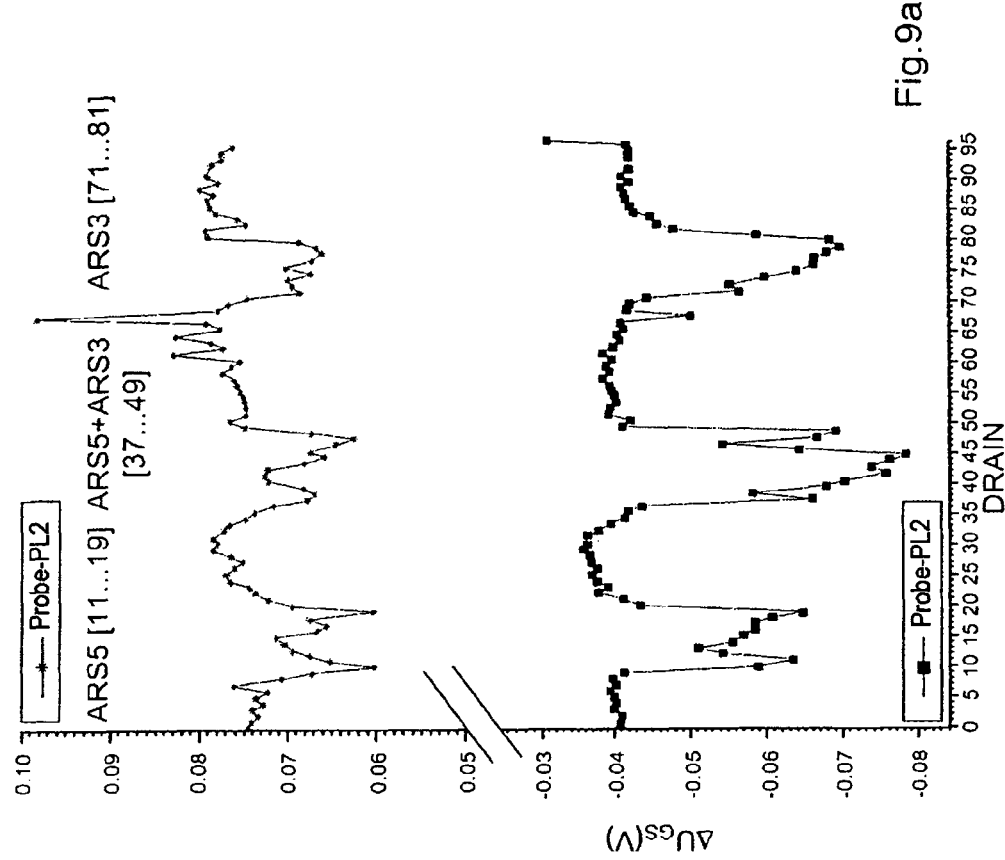

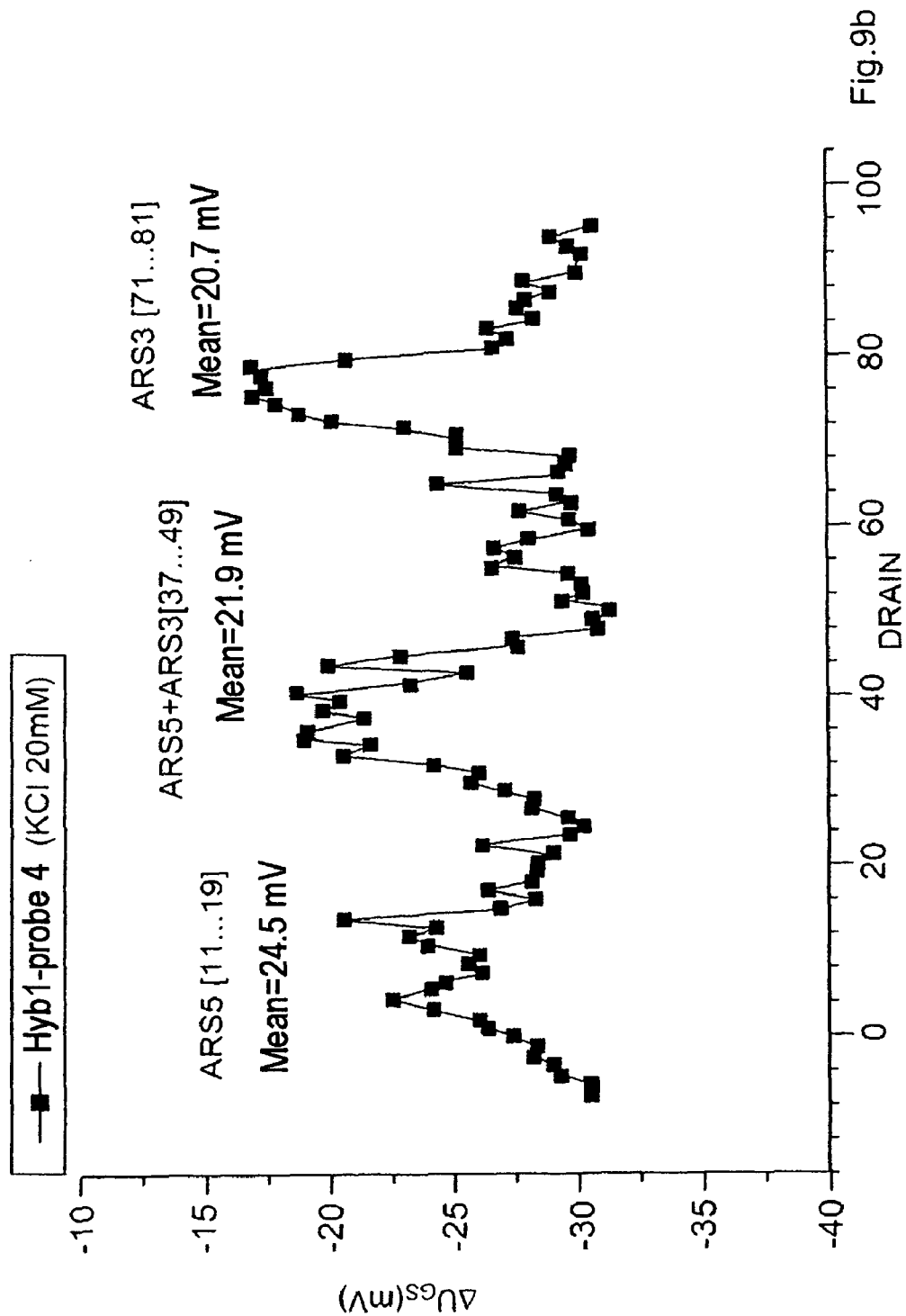

SEQUENCE LISTING

<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Synthetic DNA

<400> SEQUENCE: 1
ccgcgaactg actctccgcc                                              20

<210> SEQ ID NO 2
<211> LENGTH: 20
<212> TYPE: DNA
<213> ORGANISM: Artificial
<220> FEATURE:
<223> OTHER INFORMATION: Synthetic DNA

<400> SEQUENCE: 2
caggcgcgag ggctgacgtt                                              20

METHOD FOR ELECTRONICALLY DETECTING AT LEAST ONE SPECIFIC INTERACTION BETWEEN PROBE MOLECULES AND TARGET BIOMOLECULES

The present invention relates to a method for electronically detecting at least one interaction between molecules and target biomolecules.

A method for detecting the hybridization of DNA sequences using a field-effect transistor is already known, as was described in the article by E. Souteyrand et al., entitled "Direct detection of the hybridization of synthetic homo-oligomer DNA sequences by field effect", published in 1997 in J. Phys. Chem. B1997, 101, pages 2980 to 2985. A transistor of the ISFET ("ion-sensitive field-effect transistor") type which can be used in this type of application has been described in the article by Piet Bergveld "Development, operation and application of the ISFET as a tool for electrophysiology", published in IEEE Transactions on Biomedical Engineering, volume BME-19—No. 5, September 1972, pages 342 to 351. Indications on the manufacture of such transistor structures can be found in the article by V. Kiessling et al., entitled "Extracellular resistance in cell adhesion measured with a transistor probe", published in Langmuir 2000, 16, pages 3517-3521. Finally, a surface preparation method has been described in the article by A. Kumar et al., entitled "Silanized nucleic acid: a general platform for DNA immobilization", published in Nucleic Acid Research 2000, volume 28, No. 14, pages i to vi.

Two methods for fixing molecular probes to the surface can in particular be used in the context of the present invention. The first consists of direct synthesis on a solid phase, as described, for example, in the article by S. P. A. Fodor et al., entitled "Light-directed, spatially addressable parallel chemical synthesis", published in Science 251, pages 767 to 773 (1991). The second is the fixing of the molecules using a dilution.

In order to obtain a correct detection of the interactions between biomolecules, it is advisable to take into account a certain amount of parameters:

A—Sensitivity

It can be very good (comparable to that of detection by fluorescence), but it depends on the condition of the molecular layers on the active surfaces. For the transistor-type sensors which are used here, the required amount of biological molecules (probes and targets) is inversely proportional to the surface area of the sensor. It is therefore advantageous to miniaturize the structures, but attention must be paid to the signal/noise ratio.

B—Dynamics

The range of the various concentrations of molecule that can be measured is narrow. At low concentration, it is possible to be limited by parasitic signals (for example, it is sometimes possible to already see a signal induced by a drop of pure water that had dried on the surface). At high concentration, saturation is observed when the effective charge approaches zero.

C—Specificity

The term "specificity" is intended to mean the ability of the system to distinguish between two types of different target molecules. For hybridization between DNA molecules, for example, this difference may be a difference in the sequence of the base pairs. It is a question of optimizing the conditions (salt, temperature, duration and, optionally, pH) of the intermolecular recognition reaction such that the specific interaction (for example, the hybridization between complementary sequences) dominates with respect to nonspecific processes (for example, adsorption, nonspecific, ionic and hydrophobic interactions). These optimized conditions do not generally correspond to the best conditions for an electronic detection. For example, more salt is typically used for a specific hybridization than for an electronic detection. A compromise also has to be found for the distance of the probe molecules with respect to the surface. A small distance is favorable for the electronic detection because of electrostatic screening, but is often unfavorable for the specificity. If the probe molecules are too close to the $SiO_2$ surface, the nonspecific molecule/surface interactions can become dominant. In addition, the specific interaction between the probe and target biomolecules can be hindered by a surface that is in the vicinity (problem of accessibility or steric hindrance).

These effects depend on the molecular layers deposited on the active surface of the transistor array (and in particular on their charge state).

In the description hereinafter, an experimental approach that makes it possible to achieve the desired result has been proposed. This approach has made it possible to demonstrate a key point of the detection, which constitutes the basic idea of the present invention, namely that it was advisable to separate the recognition reaction from the detection step.

The present invention thus relates to a method for electronically detecting at least one specific interaction between probe molecules fixed to at least one active zone of a sensor and target biomolecules, characterized in that said sensor consists of an array of field-effect transistors ($T_1$, $T_2$, etc.), each of which has a source region (5), a drain region (D), and a gate region which constitutes an active zone (3) on which said specific interaction is to be detected, and in that it comprises the following steps:

a) bringing at least one active zone (3) into contact with probe molecules of a given type fixed to said active zone, b) bringing at least some of the probe molecules into contact with target biomolecules capable of interaction with said probe molecules, and performing a said interaction in a reaction buffer having a first salt concentration, c) measuring at least one point of the drain current/source-gate voltage/source-drain voltage characteristic of at least one transistor of said array to detect said specific interaction at least for a measurement point obtained in a measuring buffer having a second salt concentration that is lower than the first concentration for probe molecules having been subjected to said specific interaction. Step c can be carried out differentially between said measurement point and a reference point, in particular in a said measuring buffer, for probe molecules of the same type that have not been subjected to said specific interaction.

In general, a probe molecule is considered to be any molecule, in particular biomolecules (DNA, RNA, proteins, etc), or else chemically synthesized oligonucleotide DNA, or alternatively peptide nucleic acids (PNAs), which can be grafted onto said active surface and which can be specifically recognized by a target biomolecule.

According to a "temporal" variant, the differential measurement of step c) is carried out on the same probe molecules, before the interaction of step b).

According to a first "spatial" variant, the differential measurement of step c) is carried out between two groups of probe molecules of the same type, for example (DNA), that may or may not have the same sequences, fixed to distinct active zones, one of the groups having been subjected to the interaction of step b), and not the other.

According to a second "spatial" variant, the differential measurement of step c) is carried out with the measuring buffer on two groups of probe molecules arranged on distinct active zones, these two groups of probe molecules, that are for example of the same type, but may or may not have the same sequences, having been subjected to different specific interactions.

The probe molecules and/or the target biomolecules are, for example, DNA, RNA, PNA or protein molecules, or else small molecules such as vitamins. The reaction buffer and the measuring buffer are, for example, KCl. The salt concentration of the measuring buffer is, for example, greater than 0.002 mM and less than 20 mM, and it is, for example, greater than 0.005 mM and less than 20 mM, and in particular between 0.005 mM and 15 mM, or else between 0.01 mM and 15 mM. The concentration of the reaction buffer is, for example, between 20 mM and 1 M (molar concentration).

The method according to the invention is compatible with a conventional detection of molecular interaction by fluorescence.

The method can be characterized in that said measurement of at least one point of the characteristic uses the application of a given voltage ($U_{DS}$) between the drain and the source of at least one transistor, and also the application, in a first case, of a given voltage ($U_{GS}$) between the gate and the source of said transistor or, in a second case, of a given drain current ($I_D$), to said transistor. In the first case, the measurement of the characteristic point consists of the measurement of the drain current Id. In the second case, the voltage $U_{GS}$ is measured.

According to one variant, at least one solution which constitutes a reference or which contains target molecules is circulated through at least one micro-fluidic channel so as to bring it into contact with at least one active zone of a field-effect transistor.

It is, for example, possible to bring a reference solution (salt buffer, for example) and a solution containing target molecules successively into contact with one or more active zones, or else (in parallel) with one or more different active zones. Two solutions of target molecules can, for example, be brought into contact with one or more different active zones in parallel.

Other characteristics and advantages of the invention will emerge more clearly on reading the description hereinafter, in conjunction with the attached drawings in which:

FIGS. 7a and 7b illustrate the use of the micro-fluidic channels;

and FIGS. 8a to 8h and 9a to 9d illustrate two examples of use of the invention.

Figure 1:
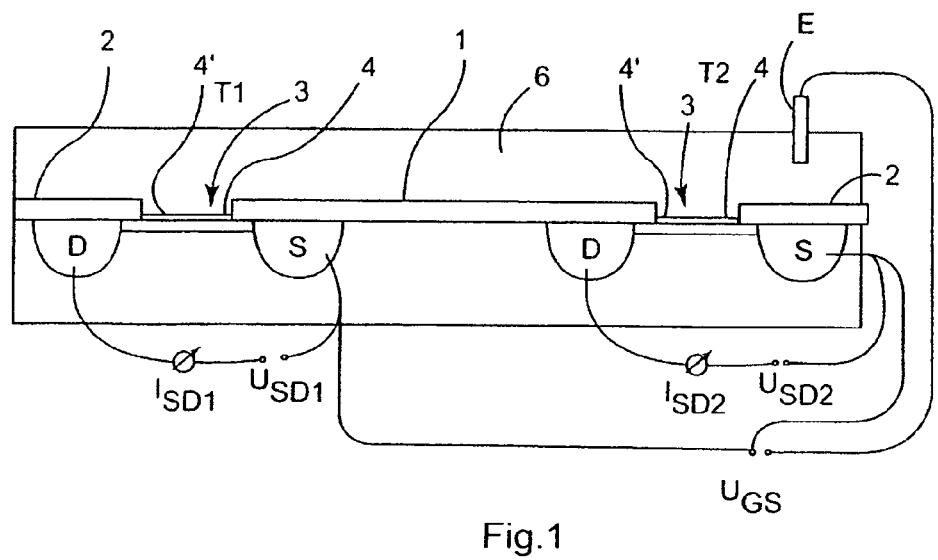
FIG. 1 represents two field-effect transistors of a detection chip comprising a plurality of such transistors organized according to a one-dimensional or two-dimensional array of transistors.
Figure 2:
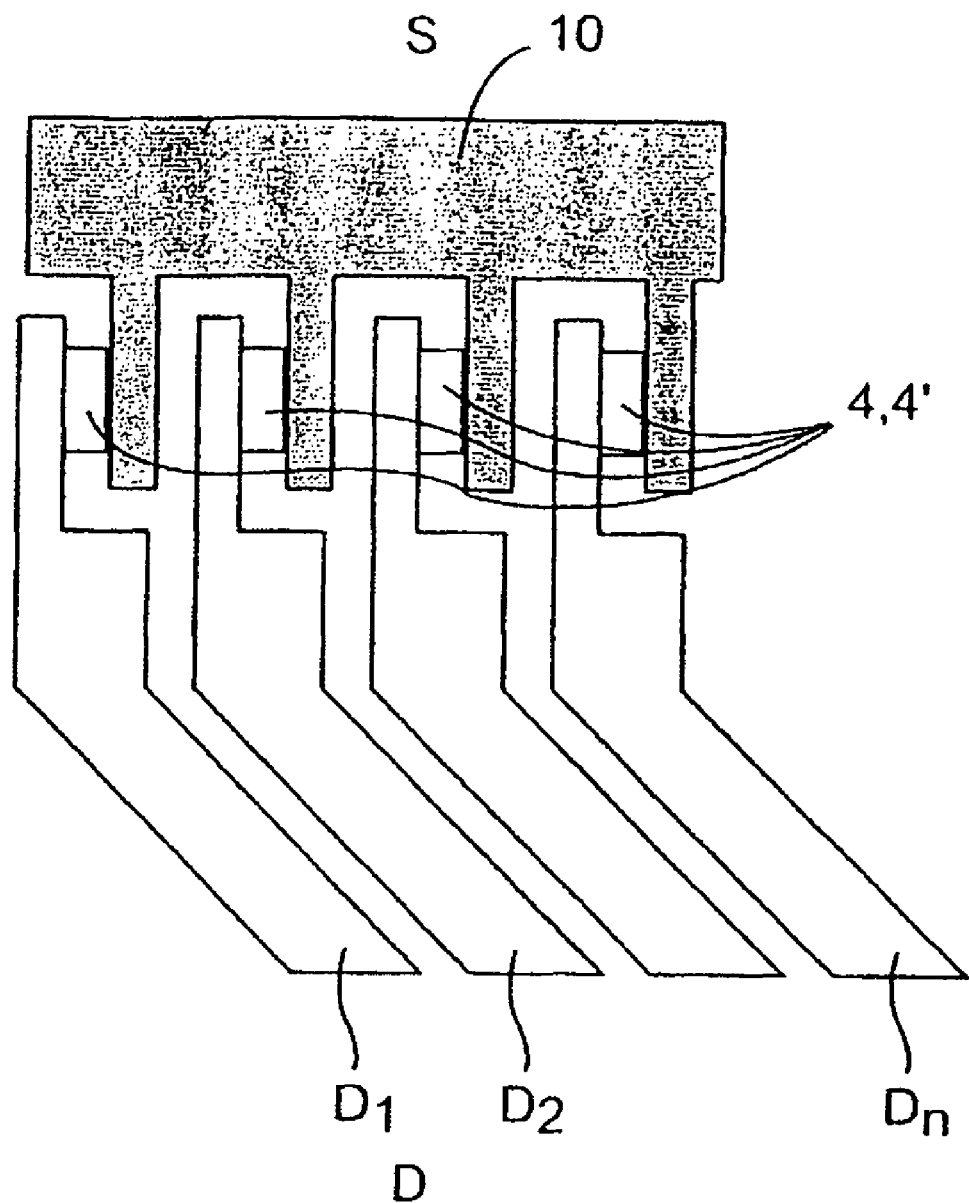
FIG. 2 represents, viewed from above, details of a detection chip and the arrangement of the active zones each corresponding to a field-effect transistor.
Figure 3:
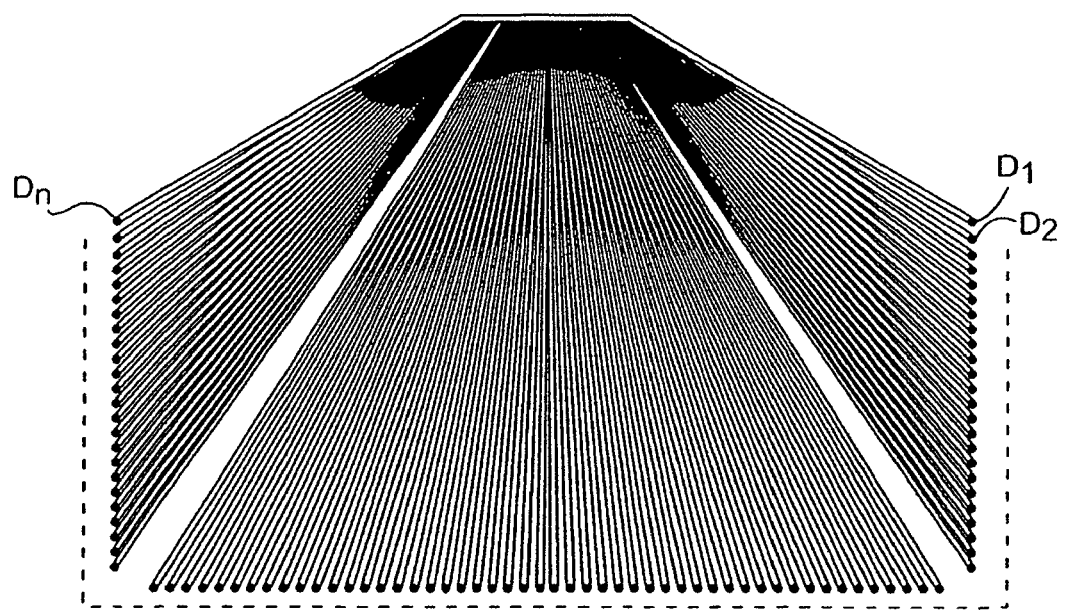
FIG. 3 illustrates the electrical drain connections of the transmissions of the one-dimensional or two-dimensional array.

FIGS. 1 to 3 illustrate a sensor having an array of field-effect transistors FET on a silicon substrate. A transistor $T_1$ or $T_2$ represented as a sectional view in FIG. 1 is provided with a source region S and a drain region D which each present an electrical contact and which are surmounted by an insulating layer respectively 1 and 2, for example an $SiO_2$ thermal oxide.

The active region 3 between the sources S and the drain D forms the gate region G of the transistor and has a thin insulating layer 4, for example a layer of thermal $SiO_2$. It is also possible not to have oxide on this active region. The active surface is then delimited by a portion 4' of the substrate which is stripped of insulating material.

Probe molecules, for example single-stranded DNA molecules, are fixed by a known method to at least some of the active surfaces 4 or 4'. For DNA, use is preferably made of depleted n-channel field-effect transistors (for which the charge carriers are electrons, which are more mobile, hence an increase in sensitivity) with a negative gate bias (i.e. the electrolyte is negatively biased with respect to the semiconductor), the DNA being negatively charged (for an electrolyte of neutral pH).

The application of a source-drain voltage $U_{SD}$ between the source S and the drain D ($U_{SD1}$ for $T_1$, and $U_{SD2}$ for $T_2$) and of a gate-source voltage $U_{GS}$ between the electrolyte 6 and the source S (for example, by means of a single Ag/AgCl electrode E) induces a two-dimensional gas of charge carriers at the Si/SiO$_2$ interface, or at the Si/electrolyte interface of each transistor. A drain current $I_D$ results therefrom, which current, for each transistor, depends substantially on the charge at the SiO$_2$/electrolyte or Si/electrolyte interface. This interface which faces the channel between the source S and the drain D is referred to as active surface.

The current $I_D$ depends on the fixing of the probe molecules, for example of the DNA molecules, to the active surface 4 or 4'.

It is possible to carry out a detection at constant source-gate voltage $U_{SG}$ and at constant source-drain voltage $U_{SD}$ by measuring the drain current $I_{Sd}$, or alternatively, as in examples 1 and 2 hereinafter, at constant drain current $I_{Sd}$ and at constant source-drain voltage $U_{SD}$ by measuring the source-gate voltage $U_{SG}$.

As shown in FIGS. 2 and 3, n structures of field-effect transistor type are integrated into a silicon substrate covered with an insulator (SiO$_2$ or other) and provided with appropriate connections (metallization or preferably doped conductive regions) by means of the electrical connections of the source 10 and of the drain ($D_1, \ldots D_n$) Unlike a standard MOS transistor structure, there is no metal gate electrode. This corresponds to the structure of ISFET (ion-sensitive field-effect transistor) type. A substrate of SOI (silicon-on-insulator) type, which provides a higher sensitivity, is preferably used.

The various structures are laterally close to one another and their active surfaces are in contact with the same measuring solution. A typical lateral dimension in current microelectronics is less than one μm. In the DNA chip technology as used in the present invention, the lateral dimension is 5-10 μm for direct synthesis on the solid phase and 50-100 μm in the case of fixing of the molecules using a dilution.

In the present parallel measurement configuration, several plots with various types of immobilized probe molecules are in contact with the same solution, in particular measuring solution, and at least one transistor structure is located below each plot. The use of several transistors per plot is possible in view of the abovementioned dimensions and permits redundancy in the detection.

An electrode E (Ag/AgCl, for example) is used to set the potential of the measuring solution 6 (electrolyte) with respect to the silicon structure that it covers and to set the operating point of the sensors (transistors). The potential of the electrolyte 6 can, in certain cases, be equal to zero. The measuring solution 6 which bathes the sensors contains ions at a concentration which gives sufficient conductivity and which does not give rise to too great a screening of the active surfaces. It preferably has a neutral pH.

The technique proposed makes it possible to facilitate the detection using various approaches.

A—Characterizing the Layers by Means of Electron Measurements

Electron measurement allows a rough characterization of the (electrostatic) states of the molecular layers deposited on the transistors. Electron measurements are carried out between the various surface preparation steps. Each chemical treatment step or molecule depositing step induces a shift in the voltage measured and the differences between the transistors reflect any possible nonhomogeneity. All these shifts then provide a characterization of the system with multiple deposited layers.

In other words, it is thus possible to verify the "electrochemical" state of the array of sensors. It is possible to compare with reference values measured for conditions that had been optimized beforehand and the aging of the structures can be monitored (for example, the degradation of the arrays by charge deposits and other effects on the $SiO_2$ oxide). In addition, comparison of two electron measurements separated by a small period of time (and, optionally, intermediate rinsing) makes it possible to verify the absence of any substantial drift in the electronic signal. These points are important since the response of the FET field-effect transistors to the immobilization of molecules on the active surface depends on all the layers on the active surface. The procedure helps to reproducibly obtain a suitable sensitivity (suitable for the amount of molecules that it is desired to detect) and a sufficient specificity.

Once the sensor array is known, the measurements can be repeated without performing further verifications.

B—Separating the Recognition Reaction from the Detection Step

The depositing of the probes, the recognition reaction and the electron measurement can be carried out in various buffers. This makes it possible to optimize these steps largely independently. The example of a hybridization with a salt concentration of 50 mM coupled to an electronic detection with a salt concentration of 0.01 mM is in particular shown hereinafter.

C—Differential Measurement

The differential approach, which is the subject of application PCT/FR02/04283, of which the present application claims the priority, is a very important element here. Compared with characterization of the layers by electron measurement, it makes it possible to detect nonhomogeneities. With respect to the separation of the recognition reaction from the detection step, it even appears to be essential, since the shift in the value of the voltage $U_{GS}$ induced by a change in buffer often shows a variation that is greater than the signal corresponding to the specific interaction that it is desired to detect.

D—Active Structures

The use of the FET field-effect structures permits a characteristic size of the order of 1 micron. The approach by alternating current AC measurement is used by Fritz et al. (Proceedings Nat. Acad. Sci., USA, Vol. 99, p. 14142 (2002)). The alternative approach of an $SiO_2$/Si passive structure with neither drain nor source (referred to as "impedance spectroscopy") requires a surface area of approximately 50 microns by 50 microns because of the parasitic capacity due to the connections [(see Wiegand et al., Review of Scientific Instruments No. 71, 2309 (2000)]. This difficulty could be bypassed through a treatment of the alternating signal in the actual chip, in the vicinity of the sensor.

Even in this case, the measurement electronics would be more complicated than those used in the context of the present invention for the direct current DC measurement based on the FET field-effect transistors. The active structures (FET) are therefore more suitable for miniaturization. By using active surface areas of 2 microns by 20 microns, the noise of the FET transistors is not limiting.

The method for detecting molecular recognitions is based on an approach by comparison, in particular differential comparison. The measurement is, for example, carried out using several transistor structures. The measurement may be differential with respect to the various types of molecules grafted and may optionally include several transistors per type of molecule. It makes it possible to compare signals before/after the interaction reaction which reveals the molecular recognition (and/or the evolution during this reaction). It will be noted that the reference measurement can be carried out in the measuring buffer having the second concentration, but also in another buffer, for example in said reaction buffer having a first salt concentration.

The method according to the invention makes it possible to circumvent the difficulties associated with the sensitivity of an individual sensor to the pH and to the ionic strengths and those associated with a variability from one individual transistor to the other (this includes the transistor structure and the quality of the fixing of the probes).

A method according to one embodiment uses the following steps:

a) homogeneous treatments of the entire insulating surface in order to prepare the fixing of the probe molecules;

b) local grafting of various types of probe molecules onto at least some of the individual active surfaces;

c) optionally, homogeneous rinsing;

d) electron measurements: the measuring electrolyte is added, the electrode is immersed and the transistors are measured (for example, one or more points of the characteristic $I_D$ as a function of $U_{SD}$ and of $U_{SG}$), and the results obtained are compared according to the transistors;

e) optionally, homogeneous rinsing;

f) addition of the solution of target molecules in the presence of electrolyte and recognition reaction;

g) optionally, homogeneous rinsing;

h) electron measurement, as (d).

Some transistors which have not been brought into contact with probe molecules (or else a single transistor) can serve as controls. Their characteristics are measured after addition of the measuring electrolyte which, for example, bathes all the transistors.

The grafting of the probe molecules is carried out by depositing microdroplets approximately 100 μm in diameter onto the active surfaces of the transistors using metal micro-pins which are commercially available, or else a commercial microdeposition system (for example, nanoplotter NP1 from the company Ge Sim).

As shown in FIG. 3, the array of n transistors (for example, n=96 transistors) has n drain connections $D_1, D_2 \ldots D_n$ and 2 connections (not represented) equivalent to the common source. The series resistances $R_c$ associated with these connections have values which depend on the index $1 \ldots n$ of the drain.

The values of these resistances $R_c$ produced, for example, by silicon doping, are not negligible, but they can be corrected.

To this effect, the drain connection resistances $R_c$ are, for example, calculated from the geometric links and cross sections of the doped lines, the resistivity of which is known. The calculation is compared with a measurement of the resistance as a function of the drain index by applying a DC voltage (for example, $U_{SD}$=0.1 V and $U_{SG}$=2 V).

Figure 4:
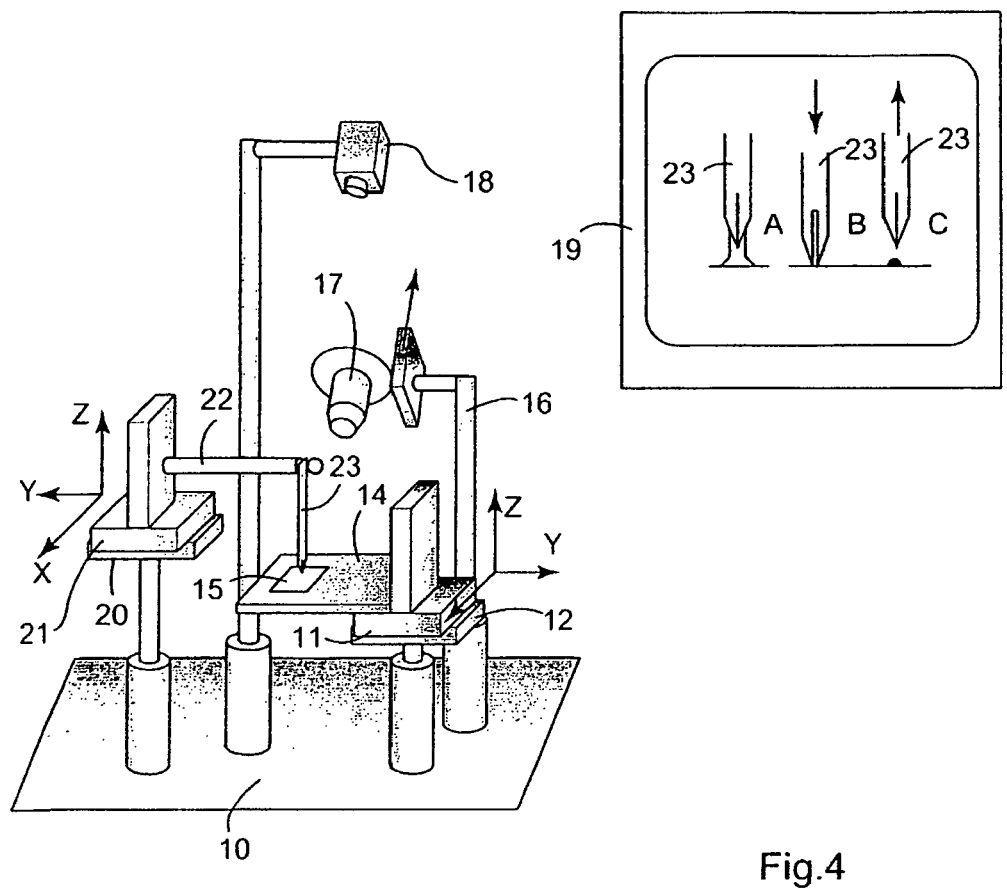
FIG. 4 represents a device for depositing the solution onto selected active zones.

An installation such as that represented in FIG. 4 can be used to implement the method: a platform 12 is placed on a table 10, said platform incorporating a control device comprising a microcontroller for a table 11 providing movement in three perpendicular directions X, Y and Z. A chip 15 incorporating the array of n transistors is placed on a support 14. Another platform 20 comprising a table 21 providing movement in the three directions X, Y and Z is used to move an arm 22 carrying a micro-pin or a pipette 23 for depositing the microdroplets onto at least some of the n transistors. An objective 17 and/or a camera coupled to a screen 19 make it possible to observe the deposition of the microdroplets and to control the operations.

Drain current $I_D$ measurements are carried out with, for example, $U_{SG}$=1 V and $U_{SD}$=0.9 V and a deposited electrolyte of neutral pH which consists of KCl at a content of 0.1 millimole per liter. Since the transistors (p-channel storage transistors) have their sources interconnected, the source voltage or the gate voltage can serve as voltage reference (for example, the mass voltage).

Before these measurements, an overall treatment of the surface of the Si/SiO$_2$ structure is performed by incubation for 1-2 minutes in sulfochromic acid and rinsing under a stream of deionized water and then incubation for 3 to 5 minutes in a solution of NaOH (60 µl 16N NaOH, 420 µl of ethanol and 220 µl of water) and, finally, rinsing under a stream of deionized water.

Figure 5A:
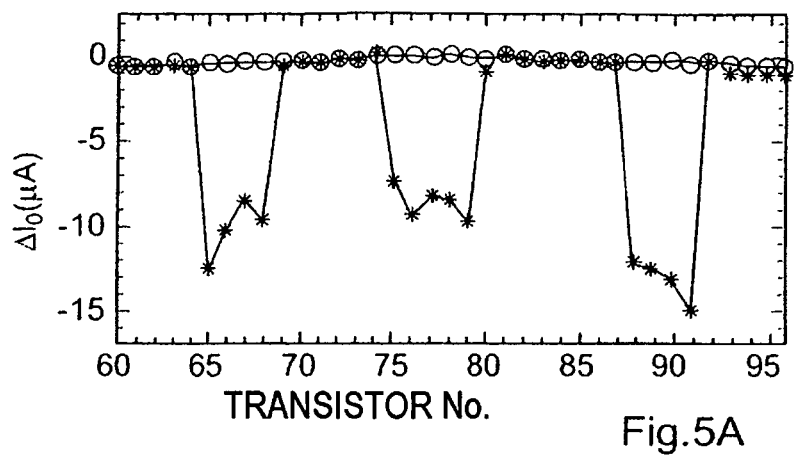
FIGS. 5a to 5c represent the results of experiments carried out under various experimental conditions.

The difference between two measurements carried out before local deposition but before and after rinsing with water is shown as small squares in FIG. 5a. The crosses represent the difference between a measurement carried out after local deposition of two different solutions and a measurement carried out before deposition (the measurement carried out before the rinsing with water).

Using a commercial pin 23 (Telechem SMP3B) mounted on the device 22 shown in FIG. 4, a solution of poly-L-lysine is deposited onto the transistors 64-69, the transistors 74-79 and the transistors 87-91.

Solution: poly-L-lysine (0.01% weight/volume "w/v" final concentration (P8920, Sigma)) in a 0.1×PBS buffer at pH 7.

After the local depositions, the sample is dried for 15 minutes in a humid atmosphere and then for 5 minutes at 50° C.

The poly-L-lysine is positive in the measuring electrolyte (neutral pH) due to the ionized amine groups. The decrease in current observed on the poly-L-lysine deposits is compatible with the adsorption of a positive charge onto the surface.

The difference in surface potential $\Delta U_{SG}$ corresponding to the measurement before/after deposition is measured. In order to determine $\Delta U_{SG}$, the two-dimensional characteristic, for example $I_D(U_{SG}, U_{SD})$, is measured and the intrinsic characteristics of the 96 transistors are determined by numerically correcting the characteristics measured as a function of the resistances $R_c$ of the drain lines in series. The modification of the condition of the SiO$_2$ interface induces a change in the intrinsic characteristic which corresponds to a shift $\Delta U_{SG}$ at constant $U_{SD}$ and constant drain current $I_D$. This shift makes it possible to directly obtain an independent measurement of the operating point of the transistor, unlike the change in current $\Delta I_D$ presented in FIG. 5a. The value $\Delta U_{SG}$ makes it possible, in first approximation, to quantify the change in the SiO$_2$/liquid interface induced by the local deposit. According to a variant, $U_{SG}$ is varied so as to keep $I_D$ constant.

Figure 5C:
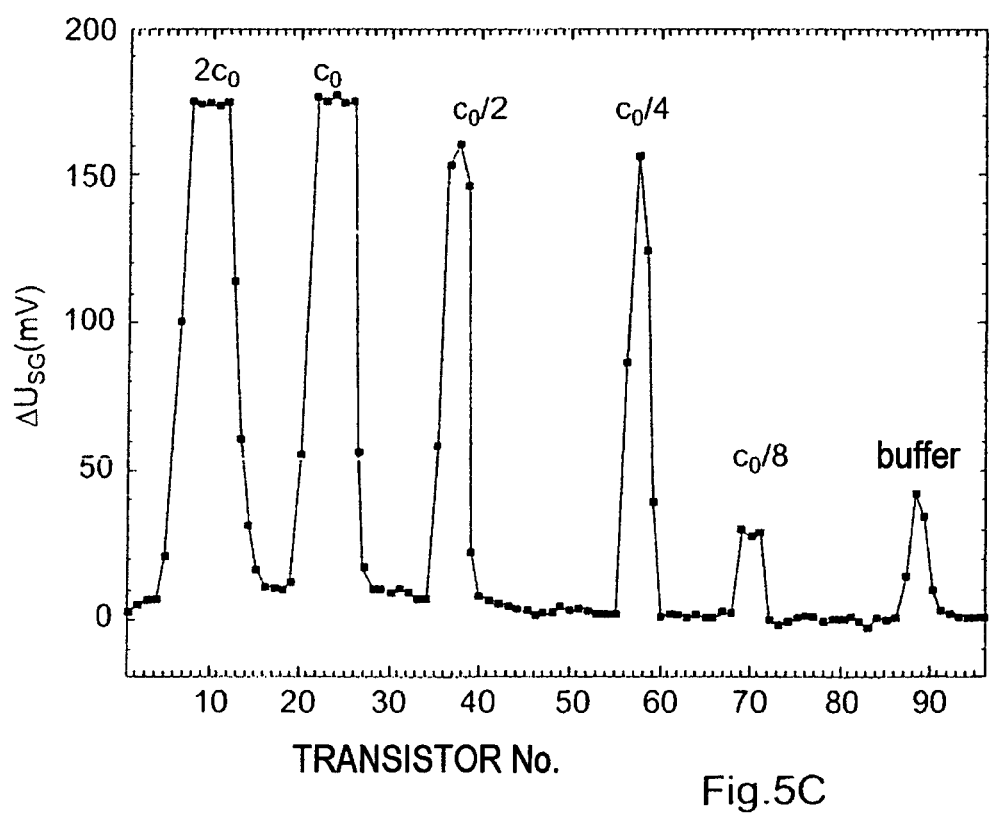
Figure 5B:
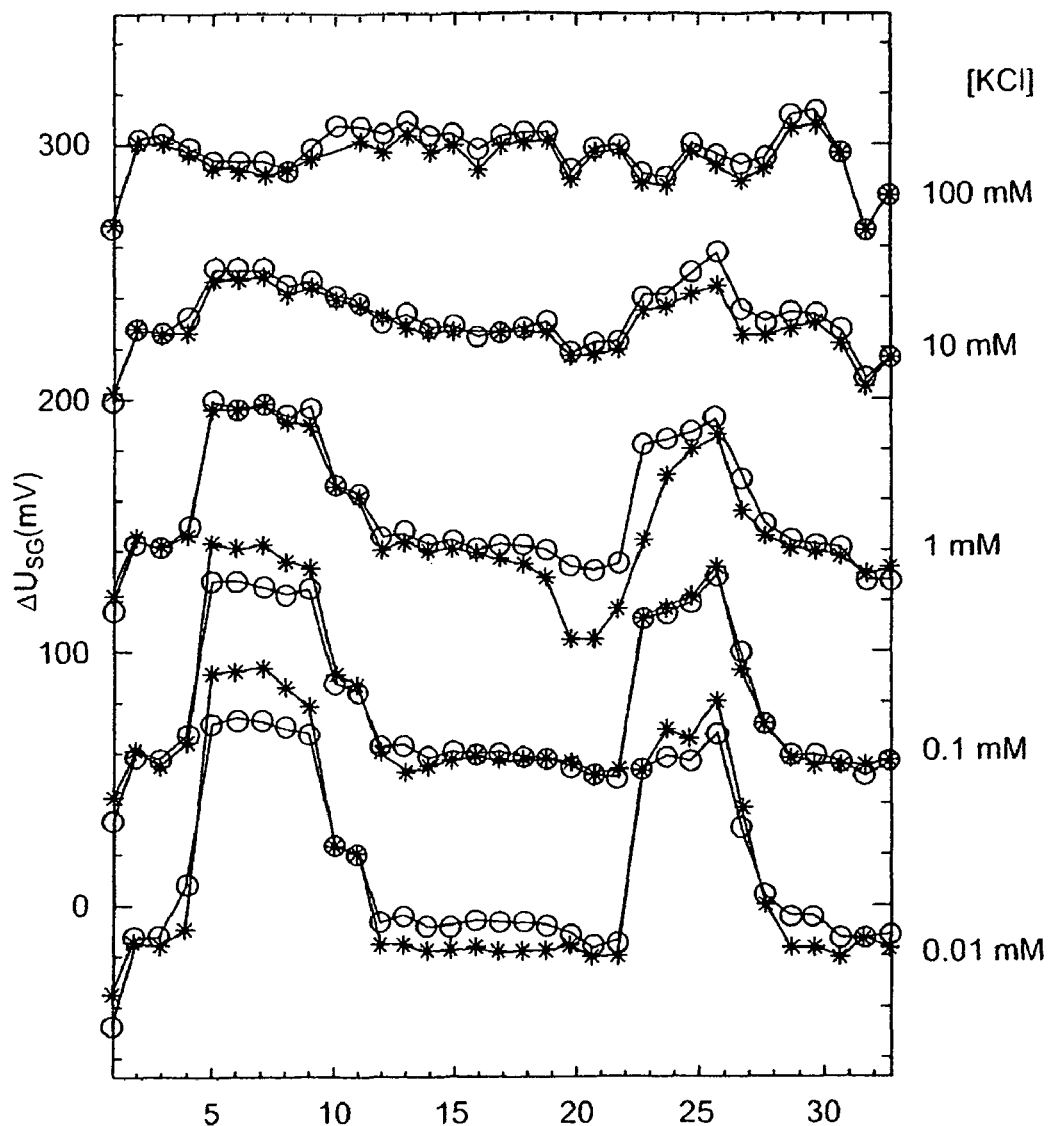

FIGS. 5a to 5c show differential measurements carried out before and after deposition of poly-L-lysine (FIG. 5a), carried out as a function of the concentration of KCl (FIG. 5b), and carried out as a function of the concentration of deposited poly-L-lysine.

In FIG. 5a, the variations $\Delta I_D$ in the drain current $I_D$ are represented on the y-axis for each of the transistors 60 to 96 identified on the x-axis ($U_{SG}$=1 V, $U_{SD}$=0.9 V and electrolyte KCl at 0.1 mM). The differences $\Delta I_D$ between two measurements carried out before a local deposition but separated by rinsing with water are represented by circles. The differences $\Delta I_D$ corresponding to measurements carried out before and after a local deposition of poly-L-lysine are represented by stars. After the local deposition, the sample is left at ambient temperature for 15 minutes in humid medium, before being dried at 50° C. for 5 minutes. The dilution $C_o$ of the poly-L-lysine is 0.01% weight/volume "W/V" final concentration (P8920, Sigma) in 0.1×PBS buffer at pH 7.

In FIG. 5b, the differences $\Delta U_{SG}$ in the source-gate voltage $U_{SG}$ are measured on some of the transistors of an array of 62 FET transistors with $U_{SD}$=1.2 V and $I_D$=50 µA. The differences between a reference measurement (carried out before local deposition and with a concentration of KCl of 0.01 mM) and two series of measurements (carried out after local deposition of poly-L-lysine and with various concentrations of KCl) are represented by circles and stars. Here, a local deposition of poly-L-lysine was carried out in two distinct zones with the same dilution $C_o$ as in the case of FIG. 5a. In each of the two series of measurement, the concentration of KCl in the measuring buffer is varied between 0.01 mM and 100 mM, the range including the values 0.1 mM, 1 mM and 10 mM. The surface is rinsed with water between the two series of measurement. A notable sensitivity of the detection of poly-L-lysine is observed for KCl concentrations of between 0.01 mM and 1 mM, and the height of the peaks gradually decreases beyond these values.

FIG. 5c shows the variations $\Delta U_{SG}$ of the voltage $U_{SG}$ as a function of the concentration of polymer deposited (poly-L-lysine), i.e. 2$C_o$, $C_o$, $C_o/2$, $C_o/4$, $C_o/8$, in a 0.1×PBS buffer, pH 7, $C_o$ having the value indicated for the measurements in FIG. 5a. The measuring conditions are as follows: $U_{SD}$=1 V, $I_D$=100 µA, and a concentration of 0.01 mM for KCl. These measurements show that there is no advantage, under the experimental conditions chosen, in increasing the concentration beyond $C_o$.

Figure 6A:
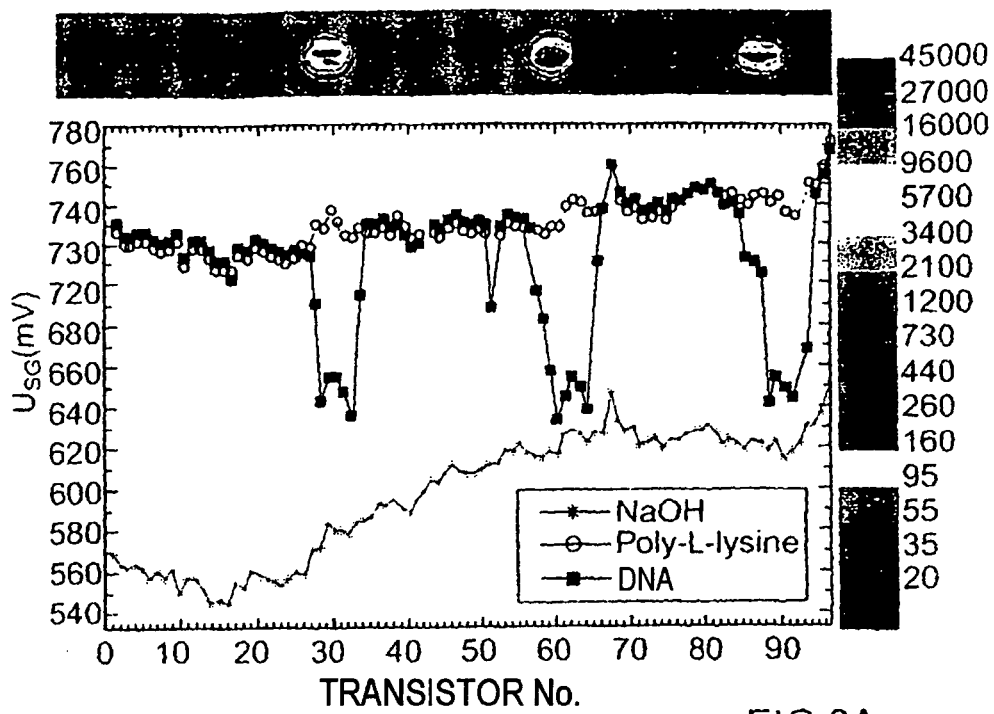
FIGS. 6a and 6b show an electronic detection of DNA.
Figure 6B:
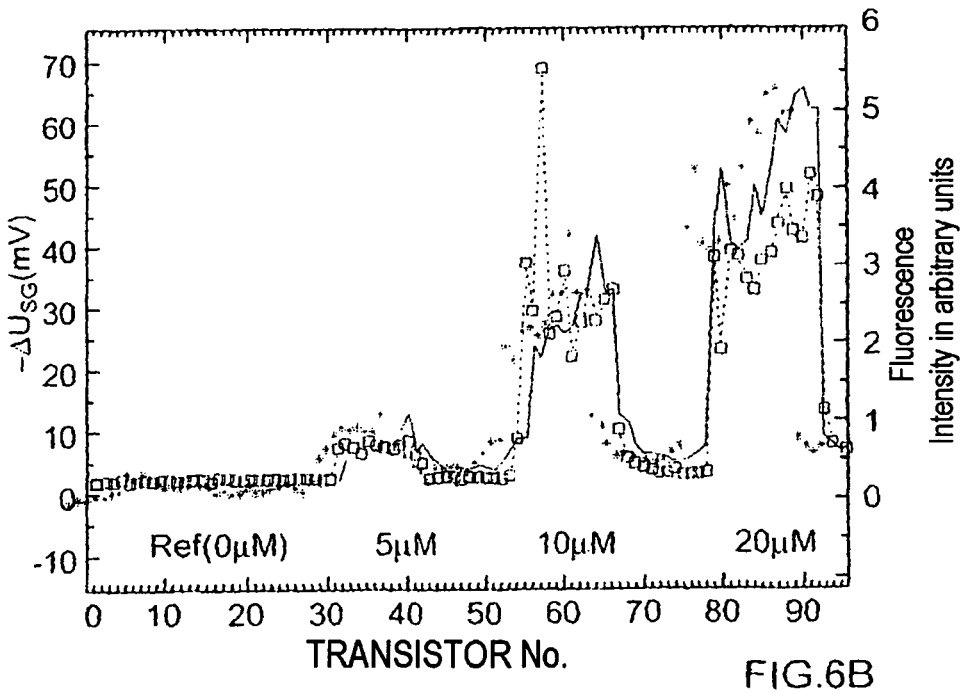

FIGS. 6a and 6b show the electronic detection of DNA. The voltages $U_{SG}$ and the variations $\Delta U_{SG}$ in the voltage $U_{SG}$ correspond to an operating point $U_{SD}$=1 V, $I_D$=100 µA, and a KCl concentration of 0.01 mM. They are obtained from the characteristic $I_D(U_{SG}, U_{SD})$ and are recorded on the curves with the FET transistor number (1 to 96) on the x-axis.

The stars represent the measurement after initial surface treatment with sodium hydroxide. The circles represent the measurement after incubation of poly-L-lysine on the entire array. In order to allow immobilization of DNA, the array of FET transistors is incubated for 30 minutes in a dilution of poly-L-lysine (concentration Co). Next, without any prior drying, rinsing is carried out with water, followed by air-drying. The incubation results in shifts in the voltage $U_{SG}$ by a value of 97±50 mV (statistical value over 67 surfaces prepared), which reduce the variations between transistors in the electronic signal. These shifts are compatible with those observed with the values measured in relation to FIG. 5c on local deposits at the same concentration. The squares represent the measurements after local deposition of oligonucleotides (5' Cy-5 modified 20-mer, concentration 50 µM in deionized water) around the transistors Nos. 30, 60 and 90. The microfluorescence image of the abovementioned three DNA points is represented in level of gray and above FIG. 6a.

FIG. 6b shows the electronic detection and detection by fluorescence of Cy5 modified oligonucleotides. The points represented by stars were obtained by the difference $\Delta U_{SG}$ between two electron measurements carried out before and after 4 local depositions with different concentrations of DNA (ref.=0 µM, 5 µM, 10 µM, 20 µM). They show the variation $\Delta U_{SG}$ in the voltage $U_{SG}$ which is observed in the characteristics of the transistors and which is due to the local deposits of DNA. The squares show the intensity of the fluorescence measured on the dried FET transistors, once the electron measurement has been carried out with the electrolyte. It will be noted that the same electronic detection is obtained with oligonucleotides of the same type, but which are not modified.

Figure 7B:
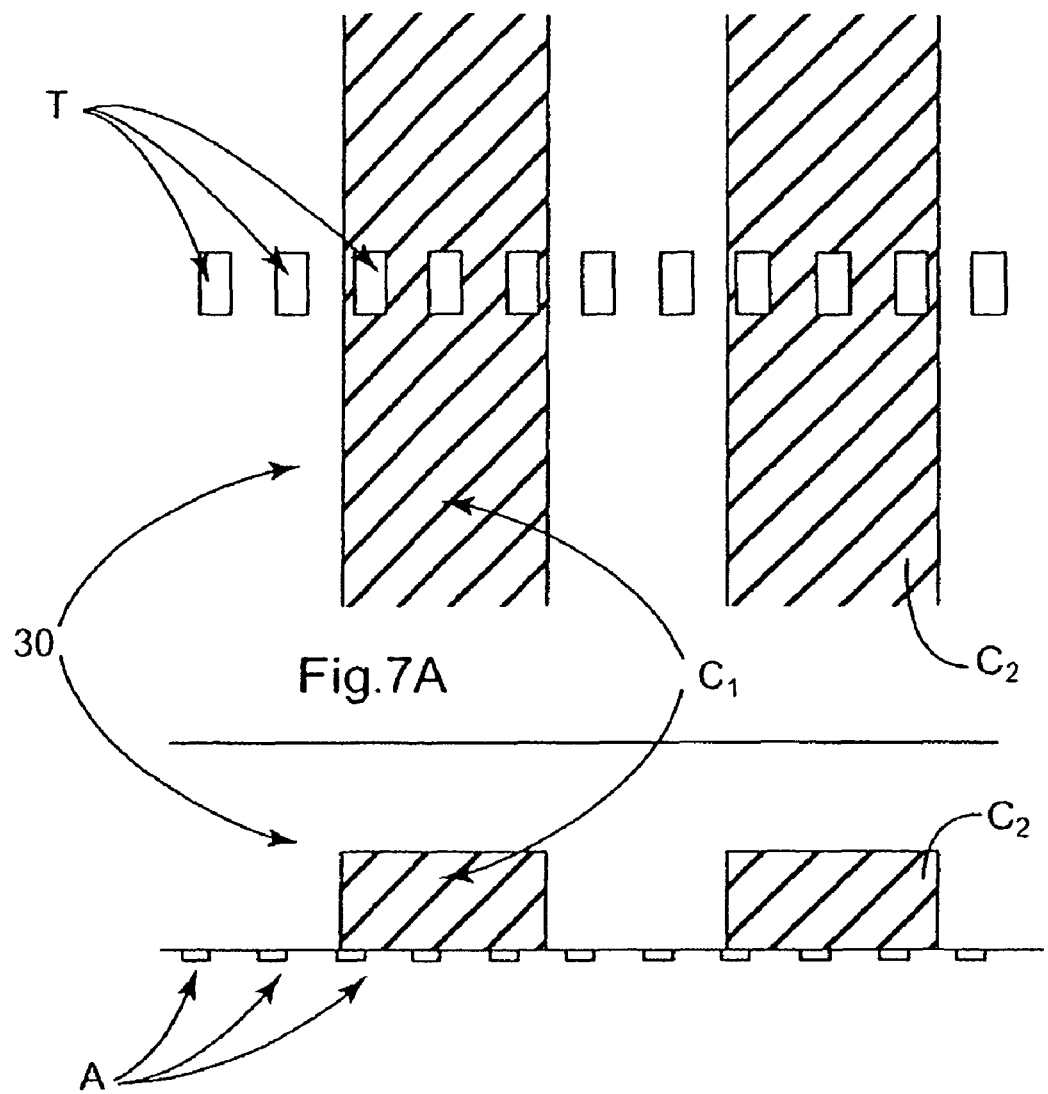

FIGS. 7a and 7b show an integrated circuit having transistors T arranged along a line (or several lines). Two microfluidic channels (for example parallel) $C_1$ and $C_2$ of a substrate 30 make it possible to bring one or more field-effect transistors T into contact with a reference solution or a solution containing target molecules which circulate in a channel $C_1$ and/or $C_2$. The material of a substrate 30 which comprises the microfluidic channels (or capillaries) can be a PDMS (polydimethylsiloxane) polymer or the like, a glass, silicon, etc.

It is thus possible to carry out differential measurements using two solutions which circulate in the two channels $C_1$ and $C_2$. It is also possible to prepare a large number of such microfluidic channels on the same substrate 30, the substrate in which they are arranged being interlinked with the semiconductor substrate into which the FET field-effect transistors are integrated. It is also possible to measure a variation inside a given channel. This variation may be over time. It is also possible to inject various solutions into a capillary, and the concentration profile remains unchanged along the channel, even far from the point of injection. Reference will be made to the article by Paul J. A. Kenis et al., entitled "Microfabrication inside capillaries using multiphase laminar flow patterning", published in Science, vol. 285, Jul. 2, 1999, pp. 83-85 (in particular FIG. 1a).

An analytical technique using microfluidics is described in the article "Monolithic integrated microfluidic DNA amplification and capillary electrophoresis analysis system" by Eric T. Lagally et al., published in Sensors and Actuators B 63 (2000), pp. 138-146.

The detection of at least one specific interaction between probe biomolecules and the target biomolecules is advantageously carried out by using a measuring buffer for which the salt concentration (for example, KCl) is lower than that of the reaction buffer.

The biomolecules concerned (sources or targets) can, for example, be DNA, RNA, proteins and vitamins.

The specific interactions can, for example, be DNA-DNA, DNA-RNA, DNA-protein, RNA-protein, protein-protein or else vitamin-protein interactions. The DNA can be chemically synthesized oligonucleotide DNA. Inter-actions can also be carried out with a peptide nucleic acid "PNA".

Additional measuring steps have been added in order to verify the surface condition of the sensor (FET transistors), the quality of the fixing of the probe biomolecules and the reproducibility of the measurements.

EXAMPLES

Products

NaOH: 60 microliters of 16N NaOH, 420 microliters of ethanol, 220 microliters of water. PLL: solution of poly-L-lysine, P8920 (Sigma), 0.01% w/v in a 0.1×PBS buffer. Oligonucleotide ARS3: 5' CCG CGA ACT GAC TCT CCG CC (SEQ ID NO: 1); Oligonucleotide ARS5: 5' CAG GCG CGA GGG CTG ACG TT (SEQ ID NO: 2); Oligonucleotide Cy3-ARS3sense: (complementary to ARS3 and with Cy3 fluorophore) Oligonucleotide Cy5-ARS5sense: (complementary to ARS5 and with Cy5 fluorophore).

Example 1

Hybridization in a 50 mM KCl Buffer and Measurement with a 0.01 mM KCl Buffer

The example shows that it is possible to obtain higher signals by decreasing the salt concentration of the measuring electrolyte compared with that of the hybridization. The specific hybridization is verified by means of a control measurement by fluorescence.

1. Overall Treatment of the $SiO_2$ Surface
   Incubation for 1 minute in sulfochromic acid, and then rinsing in a stream of deionized water, and drying with compressed air. This cycle of incubation, rinsing, drying is repeated once.
   Incubation for 4 minutes in the NaOH solution.
   Rinsing with water and drying.
2. Electron Measurement after NaOH Treatment
   Measuring buffer: KCl at a concentration of 0.01 mM (see FIG. 8a).
   This measurement is followed by rinsing with water and drying.
3. Overall Poly-L-Lysine Treatment
   Incubation is carried out for 2 h.
   This incubation is followed by rinsing with water and drying.
4. Electron Measurement "PL1"
   Measuring buffer: 0.01 mM KCl (see FIG. 8a).
   This measurement is followed by rinsing with water and drying.
5. Electron Measurement "PL2"
   Measuring buffer: 0.01 mM KCl.
   This measurement is followed by rinsing with water and drying.
   The aim of this second measurement is to verify the stability of the measurement at this stage.
6. DNA Probe Deposition
   0.2 Microliters of a solution containing the oligonucleotide Ars5 is deposited onto the left portion of the FET array, with a micropipette. 0.2 Microliters of a solution containing the oligonucleotide Ars3 is deposited onto the right portion of the array. In the two cases, the dilutions contain 1 micromole of oligonucleotide in a 50 mM KCl buffer. Incubation is carried out for 15 minutes, in a humid atmosphere so as to prevent drying.
   This incubation is followed by rinsing with water and drying.
7. Electron Measurement "Probe 1"
   A measuring buffer, 0.01 mM KCl, is used.
   FIG. 8b shows the differences delta $U_{GS}$ between the "probe 1" measurement carried out after deposition of the probe biomolecules and the PL2 measurement (step 5) carried out before this deposition.
   The "probe 1-PL2" curve (KCl concentration: 0.01 mM) shows a shift of 25 mV for the two regions of deposition on the left (deposition of Ars3 on the transistors 1 to 13) and on the right (deposition of Ars5 on the transistors 21 to 31). This value means that there is a sufficient concentration of probe biomolecules, that is not yet too close to saturation.

Pumping of the electrolyte is then performed, and said electrolyte is replaced with 1 ml of 50 mM KCl, without drying.

8. Electron Measurement "Probe 2"

Measuring buffer: KCl at a concentration of 50 mM.

As shown in FIG. 8b, the deposits are no longer seen.

No rinsing. An electron measurement "probe 3" is carried out (50 mM KCl) in order to verify the stability (FIG. 8c).

9. Hybridization 1 (with Cy5-Ars5Sense)

During the "probe 2" measurement (step 8), there was 1 ml of KCl on the FET transistors.

Next, 100 μl of Cy5Ars5sense are added directly (without rinsing).

The final dilution of oligonucleotides is then of the order of 100 nM. Agitation is carried out by pumping and this solution is redeposited twice. After agitation, the recognition reaction takes place for 5 minutes in the dark (so as to prevent bleaching of the fluorophores).

After 5 minutes, rinsing is performed: pumping of the electrolyte and addition of 1 ml of 50 mM KCl, agitation, followed by further pumping, etc. This cycle is repeated 3 times. These rinses stop the reaction. At no time during this step is there any drying on the surface.

10. Electron Measurement "Hyb1"

The electrode is immersed in the 50 mM KCl buffer and the electron measurement is carried out.

Figure 8D:
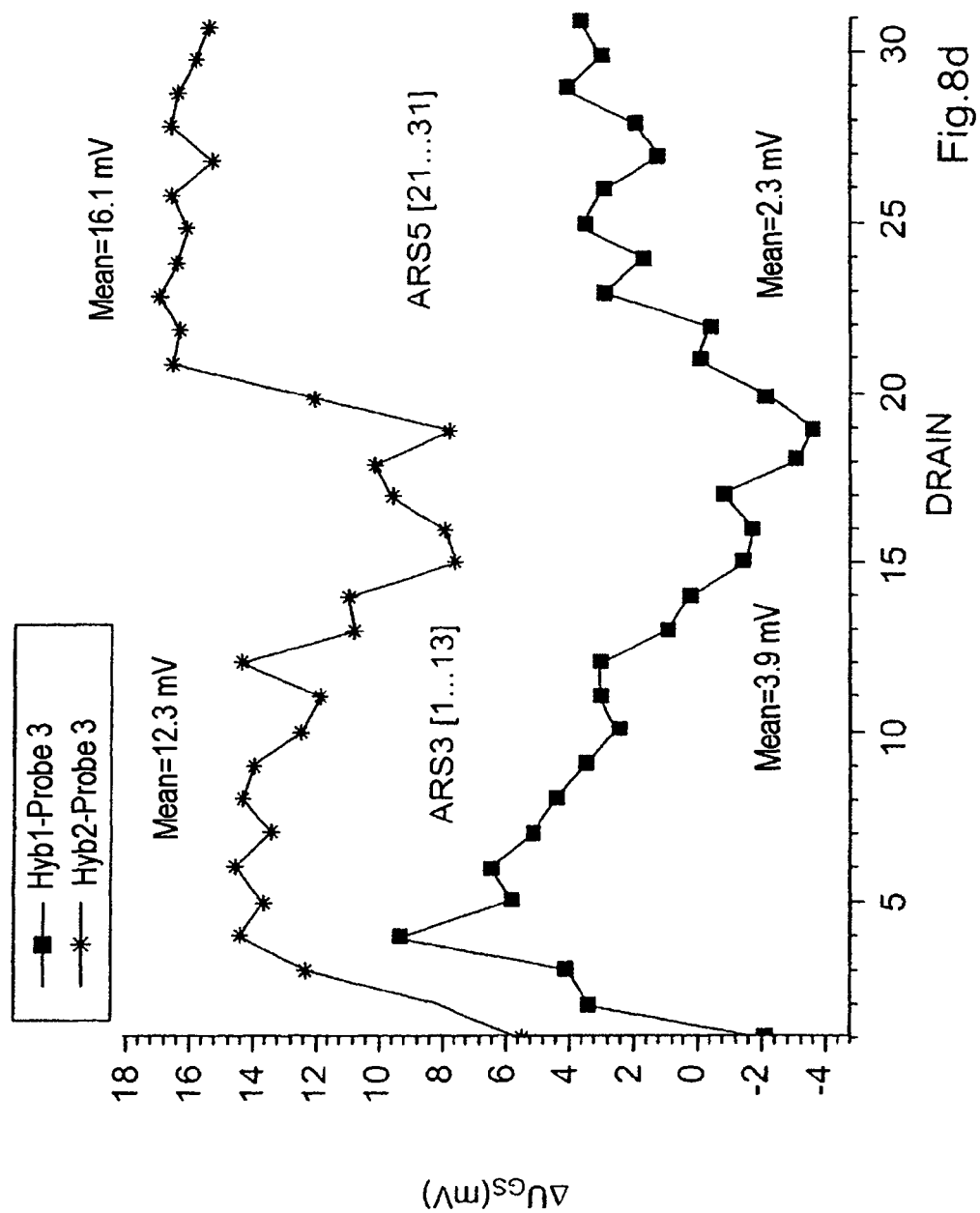

The resulting Hyb1-probe 3 curve is represented in FIG. 8d.

The shift delta $U_{SG}$ between the measurements referred to as Hyb1 and probe 3 is approximately +3.9 mV over the Ars3 region and approximately +2.3 mV over the Ars5 region (here, the probe biomolecules and the target biomolecules have complementary sequences). This shift is approximately −1.6 mV over the central region that has no DNA probe deposition (transistors 14 to 20).

After this measurement, rinsing is performed: pumping of the electrolyte and addition of 1 ml of 0.01 mM KCl, agitation, repumping, etc, repeated 5 times. At no time during this step is there any drying on the surface.

11. Electron Measurement "Hyb12"

The measuring electrode is immersed in the 0.01 mM KCl buffer and the electron measurement is carried out.

The resulting curve (Hyb12-probe 1) is represented in FIG. 8e. The shift signs correspond to those which were observed at 50 mM ("Hyb1" measurement), but the levels of these shifts are greater.

In the Ars5 (Ars3) region, a mean shift of +40 mV (+49 mV) is observed between the "Hyb12" and "probe 1" measurements, carried out at 0.01 mM KCl.

12. Hybridization 2 (with Cy3-Ars3sense)

The 0.01 mM KCl electrolyte is pumped and is replaced with 1 ml of 50 mM KCl. Next, 100 μl of 1 μM Cy3Ars3sense are added directly (without rinsing).

The final dilution of oligonucleotides is then of the order of 100 nM.

Agitation is carried out by pumping and this solution is redeposited twice. After agitation, the recognition reaction takes place for 5 minutes in the dark.

Once these 5 minutes have elapsed, rinsing is performed, followed by pumping of the electrolyte, after which 1 ml of 50 mM KCl is added. Agitation and pumping are again performed. This cycle (rinsing, agitation, pumping) is repeated 3 times. These rinses terminate the reaction. At no time during this step is there any drying on the surface.

13. Electron Measurement "Hyb2"

The electrode is immersed in the 50 mM KCl buffer and the electron measurement is carried out. The result of these measurements is represented by the Hyb2-probe 3 curve in FIG. 8d.

In FIG. 8d, the difference delta $U_{SG}$ between the above-mentioned measurements Hyb1 and probe 3 is observed to be more positive on the Ars3 region (on the left) than on the Ars5 region (on the right, where the probes and targets have complementary sequences for hybridization 1). This tendency is reversed for the difference between Hyb2 and probe 2, in accordance with the fact that, for hybridization 2, the probe and target biomolecules have complementary sequences on the Ars3 region.

After this measurement, rinsing is performed: pumping of the electrolyte and addition of 1 ml of 0.01 mM KCl, agitation, repumping, etc, repeated 5 times.

At no time during this step is there any drying on the surface.

14. Electron Measurement "Hyb22"

The electrode is immersed in the 0.01 mM KCl buffer and the electron measurement is carried out. The result is represented by the Hyb22-probe 1 curve in FIG. 8f.

The shift signs are reversed with respect to those observed at 50 mM ("Hyb2" measurement) and the signals are higher.

In the Ars5 (Ars3) region, a mean shift of −11 mV (+1 mV) is observed between the "Hyb22" and "Hyb12" measurements.

After this measurement, rinsing with water and drying are carried out.

15. Fluorescence Measurements

The specific hybridization is verified with a two-color fluorescence measuring device.

With excitation at 633 nm (Cy5), more fluorescence is observed on the Ars5 region FIG. 8h).

Figure 8G:
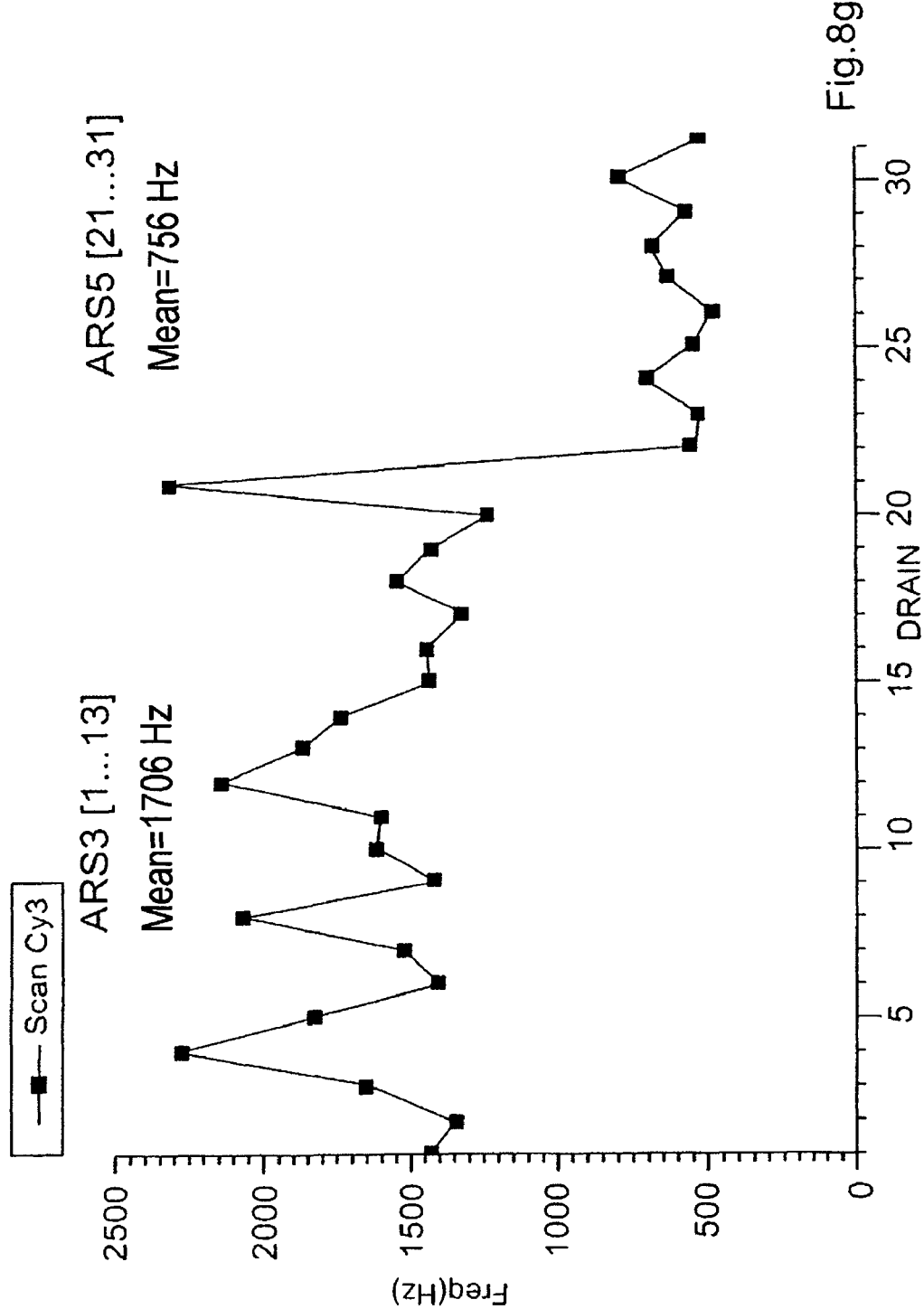

With excitation at 532 nm (Cy3), more fluorescence is observed on the Ars3 region (FIG. 8g).

Conclusion

Measurements at 50 mM and hybridization with Ars5Sense: the shift of the Ars5 region is 1.6 mV more negative than that of the Ars3 region.

Measurements at 50 mM and hybridization with Ars3Sense: the shift of the Ars3 region is 5.4 mV more negative than that of the Ars5 region.

Measurements at 0.01 mM and hybridization with Ars5Sense: the shift of the Ars5 region is 9 mV more negative than that of the Ars3 region.

Measurements at 0.01 mM and hybridization with Ars5Sense: the shift of the Ars3 region is 22 mV more negative than that of the Ars3 region.

The specific hybridization is verified by the fluorescence measurement.

Example 2

Hybridization with Microdeposition and 20 mM/0.01 mM Buffer Change

Steps 1 to 5 are identical to those in example 1.

6. DNA Probe Deposition

Using a commercial microdeposition system (GeSim, Rossendorf, Germany, Nano-plotterNP1), substantially 0.2 nl of a solution containing the oligonucleotide Ars5 is deposited on the left portion of the FET transistor array. 0.2 nl of a solution containing the oligonucleotide Ars3 is deposited on the right portion of this array. A mixture of Ars5 and of Ars3 is deposited at the center. In all cases, the dilutions contain 1 μm (1 micromole) of oligonucleotide in a buffer of deionized water. The probes dry a few seconds after the deposition at normal temperature and humidity.

No rinsing.

7. Electron Measurement "Probe 1"

Measuring buffer: 0.01 mM KCl.

The probe 1-PL2 curve in FIG. 9a shows the differences delta $U_{SG}$ between measurements carried out after the probe deposition and the PL2 measurement carried out before this deposition (with the same measuring buffer).

The "probe 1-PL2" curve shows that the deposition of the oligonucleotides induced shifts delta $U_{SG}$ of between −20 and −25 mV.

The measurement is followed by pumping of the electrolyte and replacement thereof with 1 ml of 20 mM KCl, without drying.

8. Electron Measurement "Probe 2"

Measuring buffer: 20 mM KCl.

The results are represented in FIG. 9a by the probe 1-PL2 curve (20 mM measuring buffer). The deposits are still seen, but the peaks are smaller than with the 0.01 mM measuring buffer.

No rinsing.

9. Electron Measurements "Probe 3" and "Probe 4"

Measuring buffer: 20 mM KCl.

The aim of these measurements is to verify the stability.

No rinsing.

10. Hybridization 1 (with Cy3-Ars5Sense)

During the "probe 4" measurement, there was 1 ml of KCl on the FETs. Next, 100 µl of 1 µM Cy3Ars5Sense are added directly (without rinsing). The final dilution of oligonucleotides is then approximately 100 nM. Agitation is carried out by pumping and this solution is redeposited twice. After agitation, the recognition reaction takes place for 5 minutes in the dark.

After these 5 minutes, rinsing is performed: pumping of the electrolyte and addition of 1 ml of 20 mM KCl, this cycle being repeated 3 times. These rinses terminate the reaction. At no time during this step is there any drying on the surface.

11. Electron Measurement "Hyb1"

The electrode is immersed in the 20 mM KCl buffer and the electron measurement is carried out.

The result is represented by the "Hyb1-probe 4" curve in FIG. 9b.

The shift delta $U_{SG}$ between the abovementioned Hyb1 and probe 4 measurements is approximately −21 mV over the Ars3 region (transistors 71 to 81) and approximately −25 mV over the Ars5 region (transistors 11 to 19). Here, on the Ars5 region, the probe and target biomolecules have complementary sequences.

After this measurement, rinsing is performed: pumping of the electrolyte and addition of 1 ml of 0.01 mM KCl, agitation, repumping, etc, repeated 5 times.

At no time during this step is there any drying on the surface.

12. Electron Measurement "Hyb12"

Figure 9C:
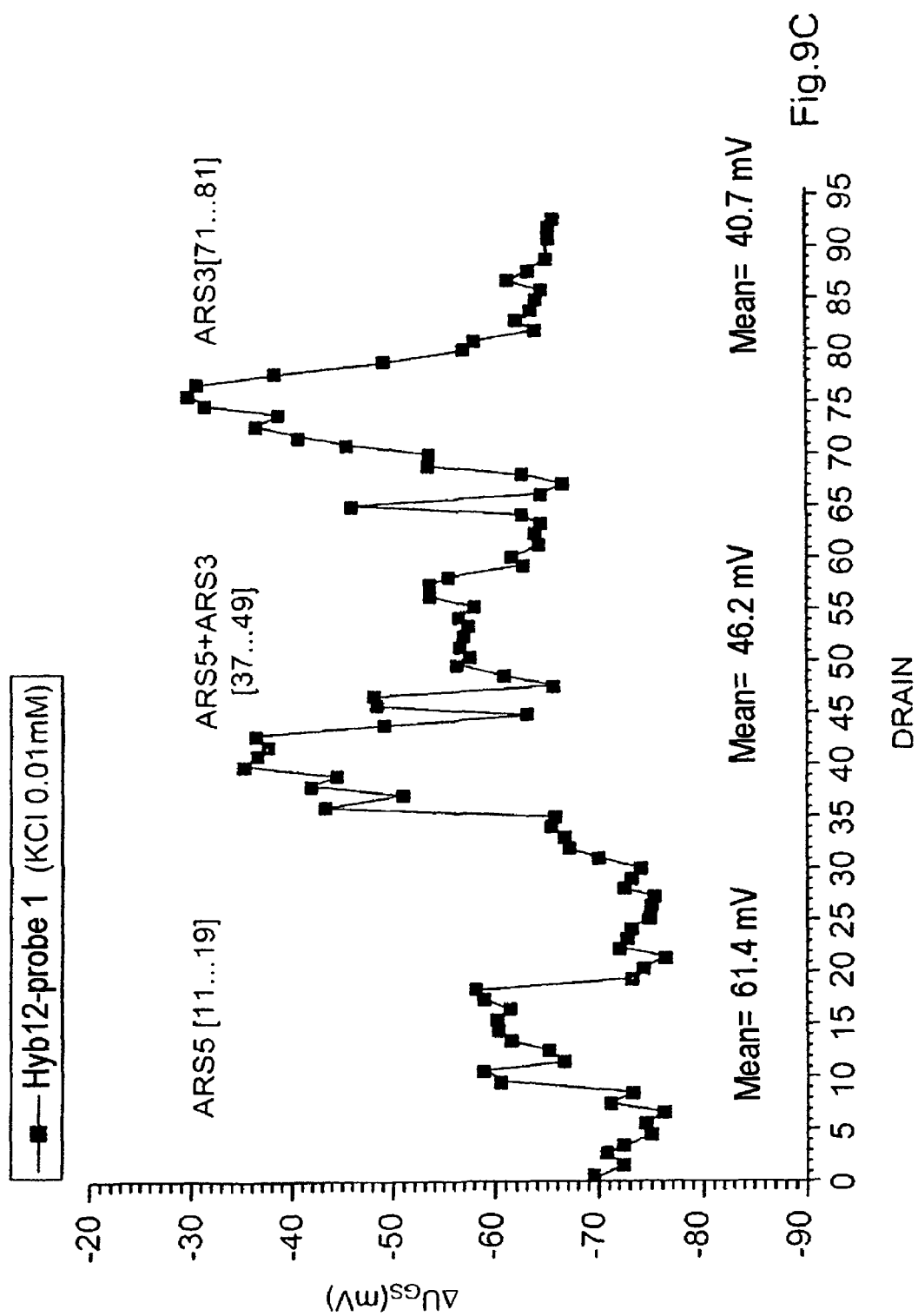
Figure 9D:
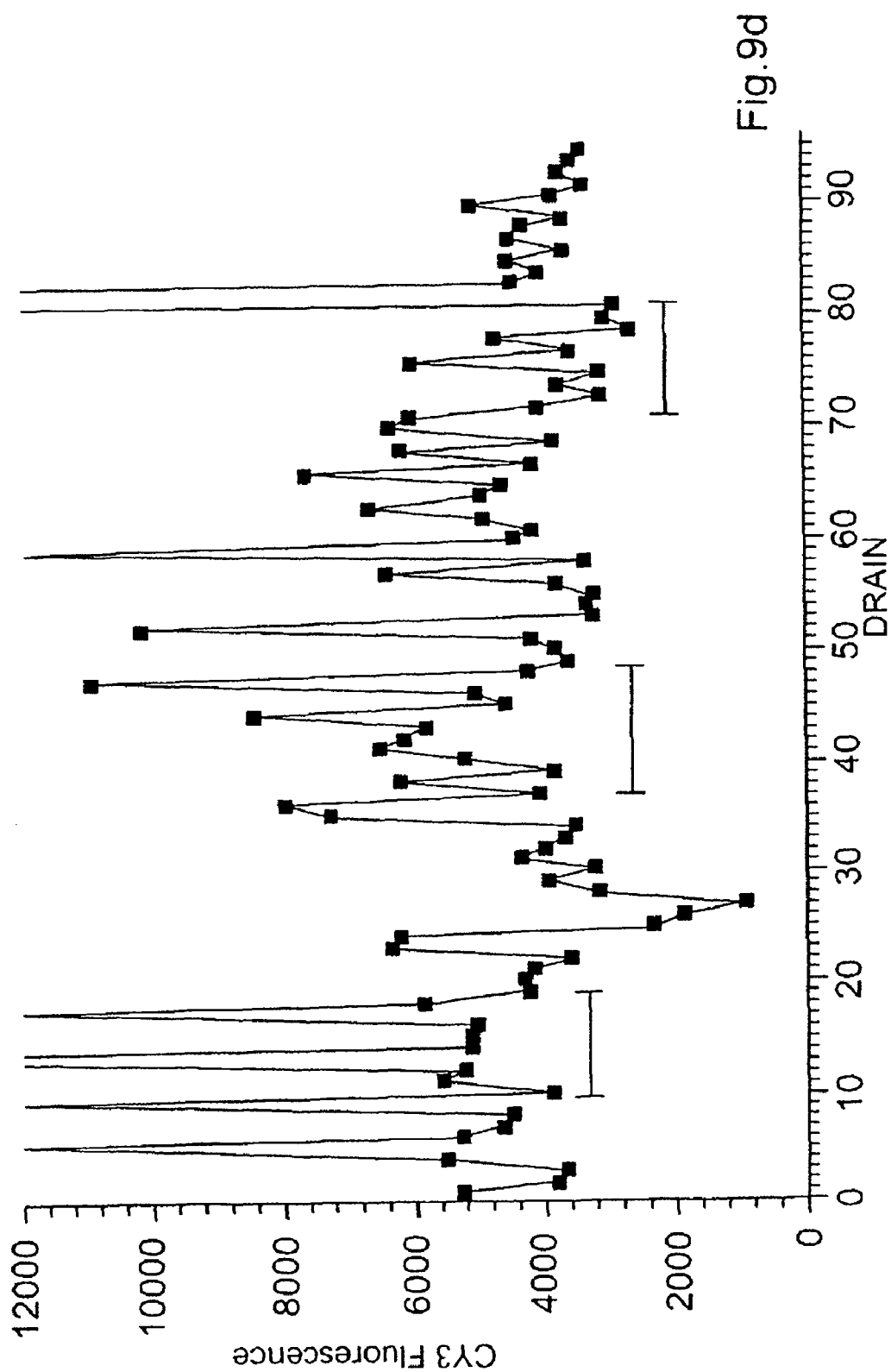

The electrode is immersed in the 0.01 mM KCl buffer and the electron measurement is carried out. The result is represented in FIG. 9c.

The shift signs correspond to those which were observed with a measuring buffer having a concentration of 20 mM, but the signals are higher.

In the Ars5 (Ars3) region, a mean shift of −61 mV (−41 mV) is observed between the "Hyb12" and "probe 1" measurements.

After this measurement, rinsing is performed: pumping of the electrolyte and addition of 1 ml of 20 mM KCl, agitation, repumping, etc, repeated 5 times. At no time during this step is there any drying on the surface.

13. Fluorescence Measurement

The specific hybridization is verified using a two-color fluorescence measuring device.

With excitation of 532 nm (FIG. 9d), more fluorescence is observed on the Ars5 region. This confirms the specific hybridization.

Conclusions

Measurements at 20 mM and hybridization with Ars5Sense: the shift of the Ars5 region is 3.8 mV more negative than that of the Ars3 region.

Measurements at 0.01 mM and hybridization with Ars5Sense: the shift of the Ars5 region is 20.7 mV more negative than that of the Ars3 region.

The specific hybridization is verified by the fluorescence measurement.

The reference measurement carried out with probe molecules that have not been subjected or not yet been subjected to an interaction with target molecules can be performed on one or more active zones distinct from that or those where a said interaction reaction with target molecules takes place. The active zones of the same integrated circuit can be used for various interactions, which makes it possible to perform, in parallel, several measurements of different types corresponding, for example, to various interactions, and/or to the study of the various target biomolecules. It is thus possible to detect several interactions with respect to one or more reference measurements carried out on probe molecules not subjected to interactions. It is also possible to detect interactions by means of comparisons between one another of measurements carried out on molecules that have been subjected to various interactions, for example between probe molecules of the same type, for example DNA, that may or may not have the same sequences, and identical or different target biomolecules.

Two examples of potential applications of the invention are given hereinafter:

One example is the study of gene expression. Interest here centers on the relative amount of the various messenger RNA molecules extracted from cells. DNA probe molecules which carry different base sequences are grafted at different sites of the surface of the chip. Each DNA probe is chosen so as to interact specifically with one type of RNA molecule (characterized by its sequence). The relative number of RNA molecules hybridized on two regions of different probes gives a relative abundance of two types of RNA molecules (and with this, the relative level of expression of the corresponding two genes). The advantage is that a large number of genes can be followed in parallel, for developmental studies, for genetic characterization of pathologies, for molecular analysis of the effect of medicinal products, etc.

Another example concerns the detection of mutations on DNA chips. Here, the intention is to analyze the DNA of a patient by investigating, in parallel, the presence (or absence) of several known mutations. For this, various oligonucleotides (typically 12-mers) are grafted at various sites of the chip. The base sequences and the hybridization conditions (salt, temperature, etc) are optimized so that the presence of a mutation (even a point mutation) induces a measurable difference in the degree of hybridization of the various probes. The target molecule sample often consists here of double-stranded DNA molecules obtained by "PCR" from a small amount of genomic DNA from the patient.

In the two cases, interest is centered on the difference in the signals induced by the hybridization of a complex sample containing a large number of different target biomolecules, on a chip with several regions of different probes (often the same type of molecule but with a different sequence). This configuration is very advantageous for electronically detecting interactions.

It is understood that the expressions "two different interactions" and "other interaction" cover the situation where this difference in interaction corresponds to two probes of different type or sequence, that are in contact with the same target molecule solution.

The detection of specific interactivity can be carried out on one or more gate regions of the FET field-effect transistor array. The advantage of using several gate regions makes it possible to demonstrate the nonhomogeneities.

Alternatively, the use of a single transistor of the array is possible for probe biomolecules of a given type and a given interaction. If a transistor with large dimensions is used, an averaged measurement of the nonhomogeneities is directly obtained.

The invention claimed is:

1. A method for electronically detecting at least one specific interaction between probe molecules fixed to at least one active zone of a sensor and target biomolecules, wherein said sensor comprises an array of field-effect transistors, each of which has a source region, a drain region, and a gate region which constitutes an active zone on which said specific interaction is to be detected, and wherein said method comprises:
   a) contacting at least one active zone with a probe molecule of a given type fixed to said active zone,
   b) contacting at least some of the probe molecules with target biomolecules capable of interacting with said probe molecules in a reaction buffer having a first salt concentration,
   c) measuring at least one point of a drain current, a source-gate voltage, or a source-drain voltage characteristic of at least one transistor of said array to detect said specific interaction at least for a measurement point obtained in a measuring buffer having a second salt concentration that is lower than the first concentration for probe molecules having been subjected to said specific interaction, said measurement being conducted spatially by means of a difference between said measurement point and a reference point, in said measuring buffer, for two groups of probe molecules fixed to distinct active zones, the measuring point being obtained for probe molecules having been subjected to the interaction of step b) and the reference point being obtained for probe molecules not having been subjected to the interaction of step b).

2. The method of claim 1, wherein said reference point is determined from probe molecules of the same type as those that were subjected to said specific interaction, and having even the same sequence or a different sequence.

3. The method of claim 1, wherein said the probe molecules subjected to said two different interactions are of the same type, whether or not they have identical sequences.

4. The method of claim 1, wherein said measuring at least one point of a drain current, a source-gate voltage, or a source-drain voltage characteristic comprises applying a given voltage ($U_{DS}$) between the drain and the source of at least one transistor, and applying, in a first case, a given voltage ($U_{GS}$) between the gate and the source of said transistor or, in a second case, a given drain current ($I_D$), to said transistor.

5. The method of claim 4, wherein, in the first case, the point is obtained by measuring the drain current $I_D$ and, in the second case, by measuring the voltage $U_{GS}$ between the gate and the source.

6. The method of claim 1, wherein the measuring buffer is KCl.

7. The method of claim 1, wherein the concentration of the reaction buffer is between 20 mM and 1 M.

8. The method of claim 7, wherein the concentration of the measuring buffer is greater than 0.002 mM and less than 20 mM.

9. The method of claim 8, wherein the concentration of the measuring buffer is at least equal to 0.01 mM.

10. The method of claim 8, wherein the concentration of the measuring buffer is at most equal to 15 mM.

11. The method of claim 1, wherein the passage between one buffer and a buffer of lower concentration is separated by a rinsing step.

12. The method of claim 1, wherein the probe molecules are molecules, in particular biomolecules, capable of being recognized by a type of target biomolecule.

13. The method of claim 12, wherein the probe molecules and/or the target biomolecules are DNA, RNA or protein molecules, or else vitamins.

14. The method of claim 13, wherein the probe biomolecules are DNA molecules and in that the field-effect transistors are of the depleted n-channel type, with a negative gate bias.

15. The method of claim 1, wherein said method further comprises, before a), at least one control measurement step with a said measuring buffer.

16. The method of claim 1, wherein said method further comprises the circulation of at least one solution which constitutes a reference or which contains target molecules through at least one microfluidic channel so as to bring it into contact with at least one said field-effect transistor.

17. The method of claim 9, wherein the concentration of the measuring buffer is at most equal to 15 mM.

* * * * *